(12) United States Patent
Kobayashi et al.

(10) Patent No.: US 9,017,264 B2
(45) Date of Patent: Apr. 28, 2015

(54) ELECTRONIC BLOOD PRESSURE METER

(71) Applicant: OMRON HEALTHCARE Co., Ltd., Kyoto (JP)

(72) Inventors: Tatsuya Kobayashi, Kyoto (JP); Yuki Yamashita, Kyoto (JP); Hiroyuki Kinoshita, Kyoto (JP); Hironori Sato, Kyoto (JP); Kenji Fujii, Kyoto (JP); Yukiya Sawanoi, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 0 days.

(21) Appl. No.: 14/350,266

(22) PCT Filed: Oct. 10, 2012

(86) PCT No.: PCT/JP2012/076231
§ 371 (c)(1),
(2) Date: Apr. 7, 2014

(87) PCT Pub. No.: WO2013/061779
PCT Pub. Date: May 2, 2013

(65) Prior Publication Data
US 2014/0257116 A1     Sep. 11, 2014

(30) Foreign Application Priority Data

Oct. 26, 2011     (JP) ................. 2011-235017

(51) Int. Cl.
*A61B 5/02*     (2006.01)
*A61B 5/021*    (2006.01)
*A61B 5/022*    (2006.01)

(52) U.S. Cl.
CPC ......... *A61B 5/02116* (2013.01); *A61B 5/02225* (2013.01); *A61B 5/022* (2013.01)

(58) Field of Classification Search
CPC ..................... A61B 5/022; A61B 5/02116
See application file for complete search history.

(56) References Cited

U.S. PATENT DOCUMENTS

| | | | |
|---|---|---|---|
| 2002/0052554 A1* | 5/2002 | Yokozeki | 600/490 |
| 2003/0097074 A1* | 5/2003 | Oka et al. | 600/490 |

(Continued)

FOREIGN PATENT DOCUMENTS

| | | |
|---|---|---|
| JP | 5-42114 A | 2/1993 |
| JP | 09-253059 A | 9/1997 |

(Continued)

OTHER PUBLICATIONS

International Search Report issued in PCT/JP2012/076231 mailed on Dec. 4, 2012 (4 pages).

(Continued)

*Primary Examiner* — Etsub Berhanu
(74) *Attorney, Agent, or Firm* — Osha Liang LLP

(57) ABSTRACT

An electronic blood pressure meter includes a cuff, an inflation control unit that controls a pump for outputting a fluid into the cuff so that a pressure in the cuff is increased at an inflation speed target in accordance with a driving voltage, a pressure detection unit that detects a cuff pressure signal indicating a cuff pressure, a blood pressure calculation unit that calculates a blood pressure value based on a pulse wave superimposed on the detected cuff pressure signal, and a target changing unit that varies the inflation speed target during an inflation process in which the cuff pressure begins to increase at an initial inflation speed target and continues to increase. The target changing unit varies the inflation speed target so that the driving voltage measured during the inflation process stays within a voltage range corresponding to a range in which the pump is capable of output.

11 Claims, 30 Drawing Sheets

(56) References Cited

U.S. PATENT DOCUMENTS

| | | | |
|---|---|---|---|
| 2011/0152650 A1* | 6/2011 | Donehoo et al. | 600/324 |
| 2012/0220884 A1* | 8/2012 | Yamashita et al. | 600/490 |
| 2012/0232412 A1* | 9/2012 | Kinoshita et al. | 600/498 |

FOREIGN PATENT DOCUMENTS

| | | |
|---|---|---|
| JP | 10-314128 A | 12/1998 |
| JP | 2001-333889 A | 12/2001 |
| JP | 2005-218582 A | 8/2005 |
| JP | 2006-129920 A | 5/2006 |
| JP | 2008-188197 A | 8/2008 |
| JP | 2009-074418 A | 4/2009 |
| JP | 2010-068922 A | 4/2010 |
| WO | 2009/142266 A1 | 11/2009 |
| WO | WO 2011058927 A1 * | 5/2011 |
| WO | WO 2011062154 A1 * | 5/2011 |
| WO | WO 2011101759 A1 * | 8/2011 |

OTHER PUBLICATIONS

Written Opinion of the International Searching Authority issued in PCT/JP2012/076231 mailed on Dec. 4, 2012 (7 pages).

* cited by examiner

| | New Set Value v for Inflation Speed Target [mmHg/s] | | | |
|---|---|---|---|---|
| | 4 | 3.5 | ... | 2 |
| Measurement Area Circumferential Length L[cm] | L(1)~L(2) | α11 | α12 | ... | α15 |
| | L(3)~L(4) | α21 | α22 | ... | α25 |
| | L(5)~L(6) | α31 | α32 | ... | α35 |
| | : | : | : | ... | : |
| | L(7)~L(8) | α61 | α62 | ... | α65 |
| | L(9)~L(10) | α71 | α72 | ... | α75 |

TB

433

| TIME | L |
|---|---|
| WT1~WT2 | L(1)~L(2) |
| WT2~WT3 | L(3)~L(4) |
| WT3~WT4 | L(5)~L(6) |
| ⋮ | ⋮ |

|  |  | Inflation Speed Target [mmHg/s] |
|---|---|---|
| Measurement Area Circumferential Length L[cm] | L(1)~L(2) | v1 |
| | L(3)~L(4) | v2 |
| | L(5)~L(6) | v3 |
| | ⋮ | ⋮ |
| | L(7)~L(8) | v6 |
| | L(9)~L(10) | v7 |

ELECTRONIC BLOOD PRESSURE METER

TECHNICAL FIELD

The present invention relates to electronic blood pressure meters, and particularly relates to electronic blood pressure meters that measure a blood pressure using pulse waves detected from a measurement area.

BACKGROUND ART

Blood pressure is one index for analyzing cardiovascular disease, and performing a risk analysis based on blood pressure is effective in preventing cardiovascular-related conditions such as stroke, heart failure, and myocardial infarction. Thus far, diagnoses have been made using blood pressure (casual blood pressure) measured at medical institutions, such as during hospital visits, health checkups, and so on. However, recent research has shown that blood pressure measured at home (home blood pressure) is more useful in diagnosing cardiovascular disease than casual blood pressure. As a result, blood pressure meters for use at home are becoming widespread.

Many household blood pressure meters employ an oscillometric blood pressure measurement technique. When measuring blood pressure using the oscillometric technique, a cuff is wrapped around a measurement area such as an upper arm, the cuff is inflated until the internal pressure thereof (a cuff pressure) reaches a pressure higher than a systolic blood pressure by a predetermined pressure (for example, 30 mmHg), and the cuff pressure is then reduced gradually or in steps. As the pressure is being reduced, a change in the volume of the artery is detected as a change in the pressure superimposed on the cuff pressure (a pulse wave amplitude), and the systolic blood pressure and diastolic blood pressure are determined based on the change in the pulse wave amplitude. Furthermore, with the oscillometric technique, it is possible to measure the blood pressure by detecting a pulse wave amplitude occurring while the cuff pressure is being increased.

To accurately detect the pulse wave amplitude in such blood pressure measurements, it is necessary to increase or decrease the cuff pressure at a constant speed using a pump or a valve. Accordingly, in Patent Literature 1 (JP 2006-129920A), feedback control is executed on a driving voltage for a pump or a valve during constant speed inflation control or constant speed deflation control based on a difference between an average speed and a target speed, so that the average speed reaches the target speed. A motor-driven pump or a piezoelectric pump can be used as the pump on which feedback control is executed. Patent Literature 2 (JP 2009-74418A), for example, discloses a piezoelectric pump structure.

Meanwhile, Patent Literature 3 (JP H5-42114A) discloses a method for determining an inflation speed based on a battery voltage.

CITATION LIST

Patent Literature

Patent Literature 1: JP 2006-129920A
Patent Literature 2: JP 2009-74418A
Patent Literature 3: JP H5-42114A

SUMMARY OF INVENTION

Technical Problem

Here, the cuff pressure and pump capabilities of a conventional electronic blood pressure meter will be described with reference to Patent Literature 1. FIG. 33 schematically illustrates a relationship between a pump output flow rate and a cuff pressure in a conventional blood pressure meter. FIG. 34 schematically illustrates a relationship between a constant speed increase in the cuff pressure and a pump driving voltage in a conventional blood pressure meter. To improve usability, smaller sizes and lower costs are in demand for household-use blood pressure meters, and the pump is small in order to meet such demands. As indicated in FIG. 33, there is a tradeoff between the size of the pump and the output flow rate of a fluid such as air from the pump.

Meanwhile, with a small-sized pump, in the case where the driving voltage undergoing feedback control so that the inflation speed matches the target speed has exceeded an upper limit voltage for driving the pump, the speed cannot be increased any more, and as a result, the cuff pressure cannot be increased at a constant speed (see FIG. 34).

Furthermore, in electronic blood pressure meters where power is supplied from a battery, the cell voltage drops during blood pressure measurement as well, and the drop in the cell voltage is greater in pumps that consume high amounts of energy. Accordingly, when using the method disclosed in Patent Literature 2, it is desirable to provide a function that enables an accurate blood pressure measurement regardless of changes in the cell voltage.

In light of this, it is an object of the present invention to provide an electronic blood pressure meter capable of accurately measuring a blood pressure regardless of changes in a voltage used to drive the electronic blood pressure meter.

Solution to Problem

An electronic blood pressure meter according to an aspect of the invention includes a cuff to be wrapped around a measurement area of a measurement subject, a pump for outputting a fluid into the cuff, a control unit that controls the pump so that a pressure in the cuff is increased at an inflation speed target in accordance with a driving voltage, a pressure detection unit for detecting a cuff pressure signal indicating a cuff pressure in the cuff, a blood pressure calculation unit for calculating a blood pressure value based on a pulse wave superimposed on the cuff pressure signal detected by the pressure detection unit, and a target changing unit that varies the inflation speed target during an inflation process in which the cuff pressure begins to increase at an initial inflation speed target and continues to increase; here, the target changing unit varies the inflation speed target so that the driving voltage measured during the inflation process stays within a voltage range corresponding to a range in which the pump is capable of output.

Advantageous Effects of Invention

According to the present invention, it is possible to accurately measure a blood pressure regardless of changes in a voltage used for driving.

BRIEF DESCRIPTION OF DRAWINGS

FIG. 15 illustrates a table referred to in order to determine an inflation speed target according to the third embodiment.

DESCRIPTION OF EMBODIMENTS

Figure 1:
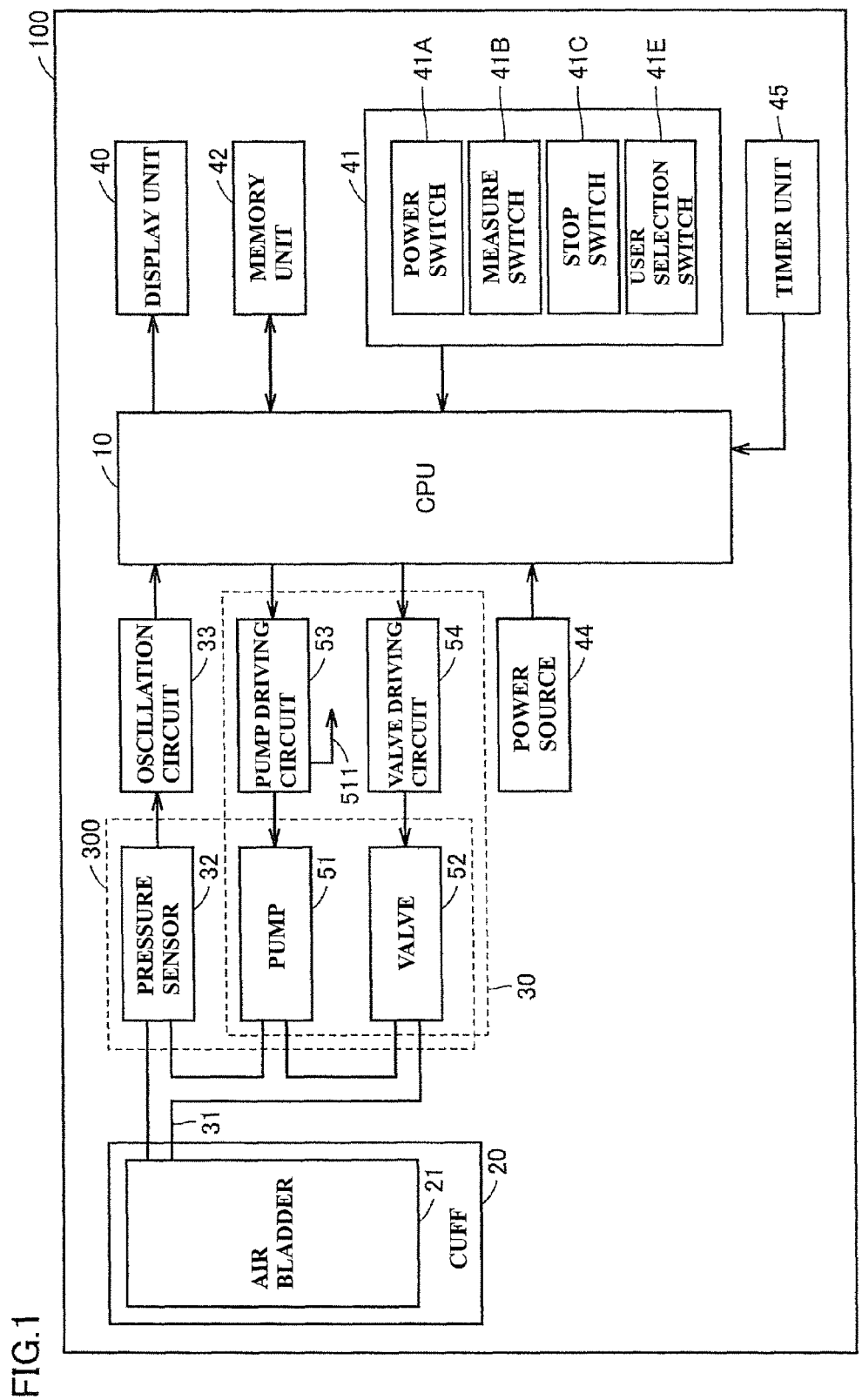
FIG. 1 is a block diagram illustrating the hardware configuration of an electronic blood pressure meter according to a first embodiment.

Hereinafter, embodiments of the present invention will be described with reference to the drawings. In the following descriptions, identical reference numerals are assigned to identical components. The names and functions thereof are also the same. Accordingly, detailed descriptions thereof will not be repeated.

First Embodiment

FIG. 1 is a block diagram illustrating the hardware configuration of an electronic blood pressure meter 100 according to the present embodiment. As shown in FIG. 1, the electronic blood pressure meter 100 includes a cuff 20 that is attached to a blood pressure measurement area and an air system 300. The cuff 20 includes an air bladder 21. The air bladder 21 is connected to the air system 300 via an air tube 31. Although the following embodiments assume that the cuff 20 is wrapped around an upper arm, which serves as the measurement area, the embodiments are not intended to be limited thereto, and the measurement area may be a wrist as well.

The electronic blood pressure meter 100 further includes a display unit 40, an operation unit 41, a CPU (central processing unit) 10 for centrally controlling various units and performing various types of computational processes, a memory unit 42 for storing programs for causing the CPU 10 to perform predetermined operations, various types of data, and so on, a power source 44 for supplying power to the respective units, and a timer unit 45 for carrying out time measurement operations. The memory unit 42 includes a non-volatile memory (for example, a flash memory) for storing a measured blood pressure.

The operation unit 41 includes a power switch 41A for accepting operations for turning the power on or off, a measure switch 41B for accepting an operation to start measurement, a stop switch 41C for accepting an operation instructing the measurement to be stopped, and a user selection switch 41E for accepting an operation that selectively specifies a user (a measurement subject). The operation unit 41 also has a switch (not shown) for accepting operations for reading out information stored in the flash memory, such as measured blood pressures, and displaying that information in the display unit.

The present embodiment assumes that the electronic blood pressure meter 100 is shared by a plurality of measurement subjects, and thus the user selection switch 41E is provided; however, in the case where the electronic blood pressure meter 100 is not shared, the user selection switch 41E may be omitted. In addition, the power switch 41A may also function as the measure switch 41B. In this case, the measure switch 41B can be omitted.

The air system 300 includes a pressure sensor 32 for detecting a pressure within the air bladder 21 (called a "cuff pressure" hereinafter), a pump 51 for supplying air to the air bladder 21 in order to increase the cuff pressure, and a valve 52 that is opened/closed in order to exhaust or inject air into the air bladder 21. The electronic blood pressure meter 100 also includes an oscillation circuit 33, a pump driving circuit 53, and a valve driving circuit 54 used for operations involving the air system 300. Here, the pump 51, the valve 52, the pump driving circuit 53, and the valve driving circuit 54 correspond to an adjustment unit 30 for adjusting the cuff pressure.

A pump that uses a motor as its driving source, a piezoelectric micro pump that uses a piezoelectric element as its driving source, or the like can be employed as the pump 51.

The pressure sensor 32 is a electrostatic capacitance-type pressure sensor, and a capacity value thereof changes based on the cuff pressure. The oscillation circuit 33 outputs a signal having an oscillation frequency based on the capacity value of the pressure sensor 32 (called a "pressure signal" hereinafter) to the CPU 10. The CPU 10 detects the cuff pressure by converting the signal obtained from the oscillation circuit 33 into a pressure. The pump driving circuit 53 controls the pump 51 based on a control signal supplied from the CPU 10. The valve driving circuit 54 controls the opening/closing of the valve 52 based on a control signal supplied from the CPU 10.

Note that the fluid supplied to the cuff 20 is not limited to air, and may be a liquid, a gel, or the like. The embodiment is also not limited to a fluid, and may instead employ uniform particles such as microbeads or the like.

Functional Configuration

Figure 2:
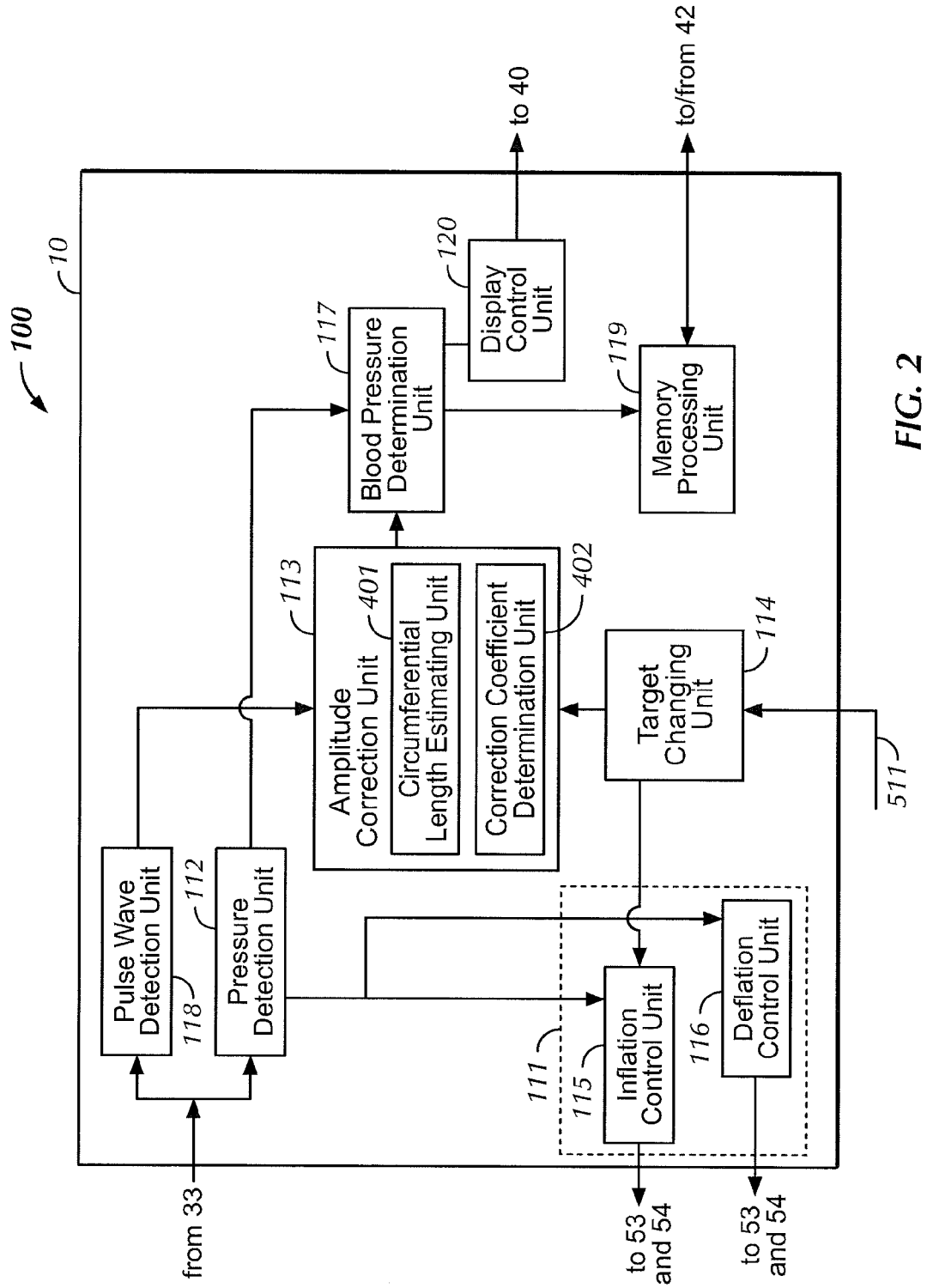
FIG. 2 is a block diagram illustrating the functional configuration of the electronic blood pressure meter according to the first embodiment.

FIG. 2 is a functional block diagram illustrating the functional configuration of the electronic blood pressure meter 100 according to the present embodiment. The functional configuration illustrates the functions provided by the CPU 10 as well as related peripheral units.

As shown in FIG. 2, the CPU 10 includes: a pulse wave detection unit 118 and a pressure detection unit 112 into which the pressure signal from the oscillation circuit 33 is inputted; an amplitude correction unit 113 for correcting a pulse wave amplitude; a target changing unit 114 that changes a target for an inflation speed (called an "inflation speed target" hereinafter) when measuring a blood pressure; an inflation control unit 115 and a deflation control unit 116 that output control signals to the pump driving circuit 53 and the valve driving circuit 54; a blood pressure determination unit 117 that determines a blood pressure value; a memory processing unit 119 for reading/writing data from/to (that is, accessing) the flash memory of the memory unit 42; and a display control unit 120 that controls the display of the display unit 40. The inflation control unit 115 and the deflation control unit 116 correspond to a driving control unit 111 for increasing the cuff pressure in accordance with the inflation speed target by controlling the driving of the adjustment unit 30 during blood pressure measurement.

The inflation control unit 115 and the deflation control unit 116 send control signals to the pump driving circuit 53 and the valve driving circuit 54 in order to adjust the cuff pressure. Specifically, control signals for increasing or decreasing the cuff pressure are outputted. In the present embodiment, the blood pressure determination unit 117 carries out a process for deriving a blood pressure as the cuff pressure is being increased at the inflation speed target. The pulse wave detection unit 118 detects a pulse wave signal expressing a change in the volume of an artery supperimposed on the pressure signal from the oscillation circuit 33, using a filter circuit. The pressure detection unit 112 converts the pressure signal from the oscillation circuit 33 into a pressure value and outputs the pressure value in order to detect the cuff pressure.

The amplitude correction unit 113 includes a circumferential length estimating unit 401 and a correction coefficient determination unit 402. The cuff 20 is wrapped around an upper arm (or a wrist), for example, serving as the measurement area. The circumferential length estimating unit 401 estimates the length of the circumference of the measurement area (that is, of the arm) around which the cuff 20 is wrapped. The correction coefficient determination unit 402 determines a coefficient for correcting the pulse wave amplitude based on pre- and post-change inflation speed targets.

The blood pressure determination unit 117 determines a blood pressure using an oscillometric technique. Specifically, the blood pressure determination unit 117 determines the blood pressure based on shifts in the pulse wave amplitude and the cuff pressure, using the cuff pressure inputted from the pressure detection unit 112 during blood pressure measurement and the pulse wave detected by the pulse wave detection unit 118 or a pulse wave whose amplitude has been corrected by the amplitude correction unit 113. For example, a cuff pressure corresponding to a maximum value of the pulse wave amplitude is set as an average blood pressure, a cuff pressure corresponding to a pulse wave amplitude on a high-cuff pressure side equivalent to 50% of the maximum value of the pulse wave amplitude is set as a systolic blood pressure, and a cuff pressure corresponding to a pulse wave amplitude on a low-cuff pressure side equivalent to 70% of the maximum value of the pulse wave amplitude is set as a diastolic blood pressure. A pulse frequency is calculated through a known procedure using the pulse wave signal. Here, the amplitude correction unit 113 and the blood pressure determination unit 117 correspond to a blood pressure calculation unit for calculating a blood pressure.

Feedback Control of Pump 51

When measuring blood pressure using the oscillometric technique, it is necessary to increase the cuff pressure at a constant inflation speed target in order to obtain an accurate measurement. In other words, when the blood pressure measurement is started, the target changing unit 114 supplies the inflation control unit 115 with an initial target speed value for inflating at a constant speed. The inflation control unit 115 calculates a speed of change in the cuff pressure based on cuff pressures that are periodically inputted from the pressure detection unit 112, compares the calculated speed of change with the inflation speed target supplied from the target changing unit 114, generates a control signal in accordance with a difference between the two based on a result of the comparison, and outputs the control signal to the pump driving circuit 53. The pump 51 undergoes feedback control in this manner so that the inflation speed reaches the inflation speed target.

Here, it is assumed that the output flow rate of the pump 51 is proportional to a voltage supplied from the pump driving circuit 53. The pump driving circuit 53 outputs a voltage signal based on the control signal to the pump 51. A voltage sensor (not shown) is provided at the output stage of the pump driving circuit 53; the voltage for driving the pump 51 is detected by the voltage sensor and a driving voltage 511 indicating the detected voltage is outputted to the target changing unit 114.

The target changing unit 114 compares the driving voltage 511 with an upper-limit driving voltage 512 that is unique to the pump 51, and when it is determined based on a result of the comparison that a condition (driving voltage 511>upper-limit driving voltage 512) is met and the pump 51 is at its maximum output with no excess capacity, the target changing unit 114 changes the inflation speed target to a lower value. The feedback control is then carried out using the changed inflation speed target. Through this, the inflation speed can be controlled to a constant speed within a range in which there is an excess margin in the output of the pump 51.

Pulse Wave Amplitude Correction

With an oscillometric technique, the accuracy of blood pressure measurement depends on the pulse wave amplitude. In the case where the inflation speed has been changed, the pulse wave amplitude includes a component of the speed of change in the cuff pressure in addition to a component of the change in the volume of the blood vessel within a single beat of the pulse, and it is thus necessary to make a correction in order to eliminate error in the pulse wave amplitude caused by the latter component. Accordingly, in the present embodiment, the pulse wave amplitude is corrected by eliminating error caused by the aforementioned change in the inflation speed target.

Figure 3:
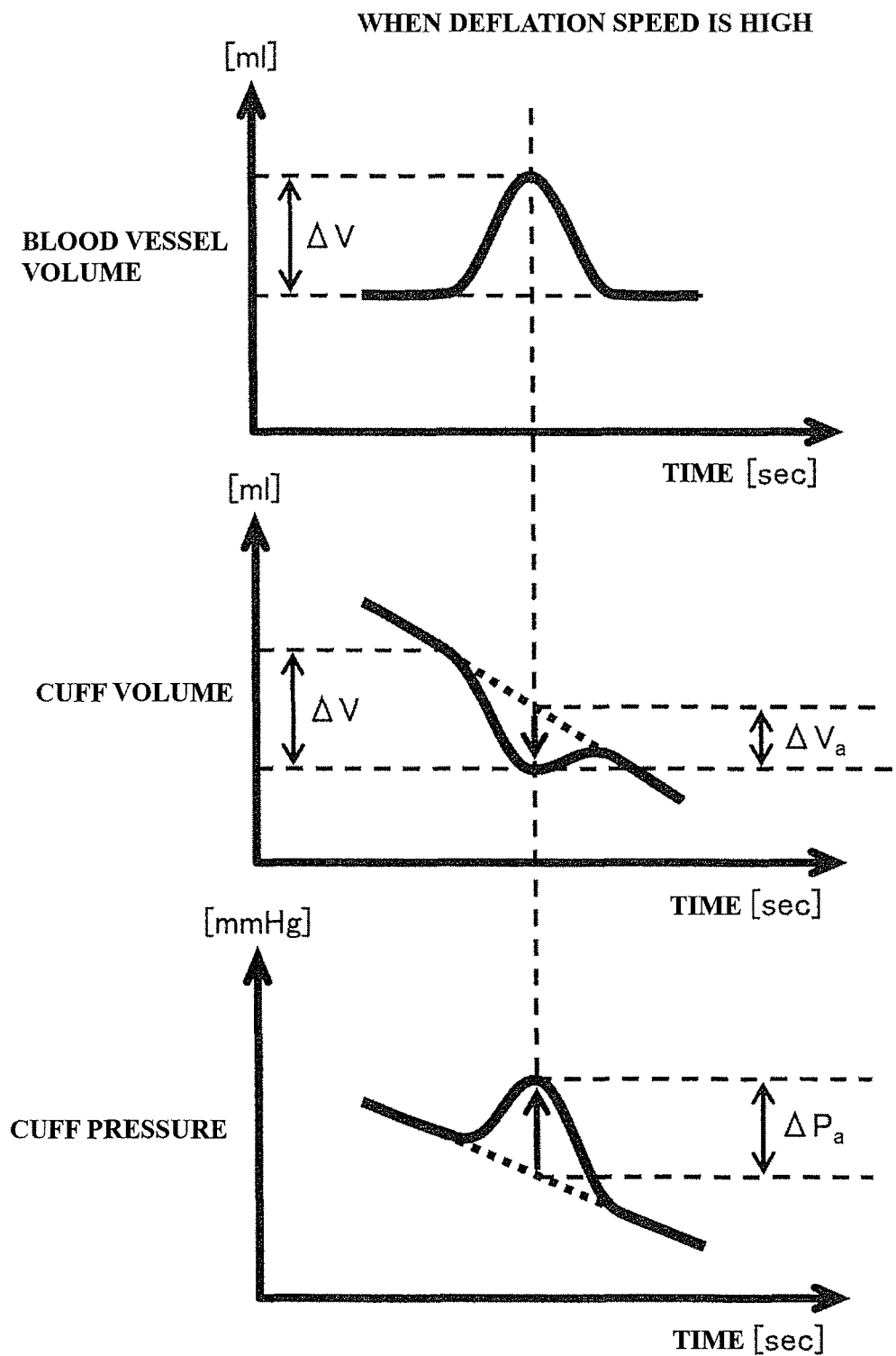
FIG. 3 is a diagram illustrating the influence of inflation speed on a pulse wave amplitude and pulse wave amplitude correction.
Figure 4:
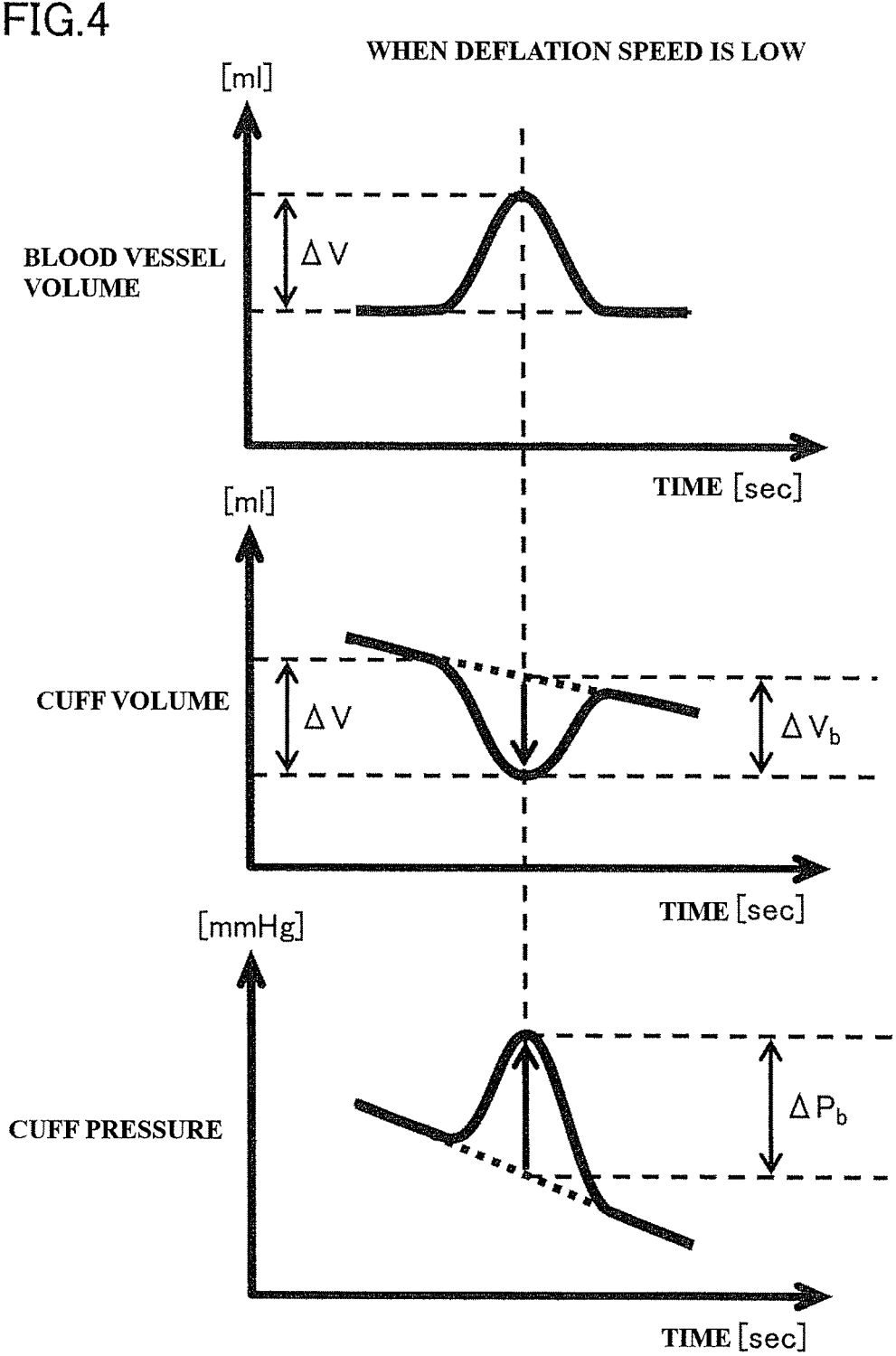
FIG. 4 is a diagram illustrating the influence of inflation speed on a pulse wave amplitude and pulse wave amplitude correction.

Here, the influence of the inflation speed on the pulse wave amplitude and amplitude correction will be described with reference to FIGS. 3 and 4. FIGS. 3 and 4 show data obtained by experiments carried out by the inventors, and indicate the influence of the deflation speed on the pulse wave amplitude during the process of deflation. Note that the principles indicated in FIGS. 3 and 4 can be applied in the same manner to the process of inflation as well.

In FIGS. 3 and 4, the lower section indicates a change in the cuff pressure over time, the middle section indicates a change in the cuff volume over time, and the upper section indicates a change in the volume of the artery/blood vessel in the measurement area over time, for cases where the deflation speed is high and where the deflation speed is low, respectively. The diagrams indicate changes occurring in the same period. Although a volume change $\Delta V$ in the blood vessel caused by heartbeats is the same between FIGS. 3 and 4 as indicated in the upper section, a maximum value of a cuff volume change relative to a baseline of the cuff volume waveform (indicated by a dotted line) differs depending on the deflation speed, as indicated in the middle section (in other words, $\Delta Va < \Delta Vb$). This volume change appears as a change in the cuff pressure, resulting in a greater volume change in the cuff 20 as the deflation speed decreases; accordingly, the change in the cuff pressure also differs, as indicated in the lower section (in other words, $\Delta Pa < \Delta Pb$). As a result, even in the case where the blood vessel volume changes in the same manner, the detected pulse wave amplitude will differ depending on the deflation speed or the inflation speed.

Figures 5, 6:
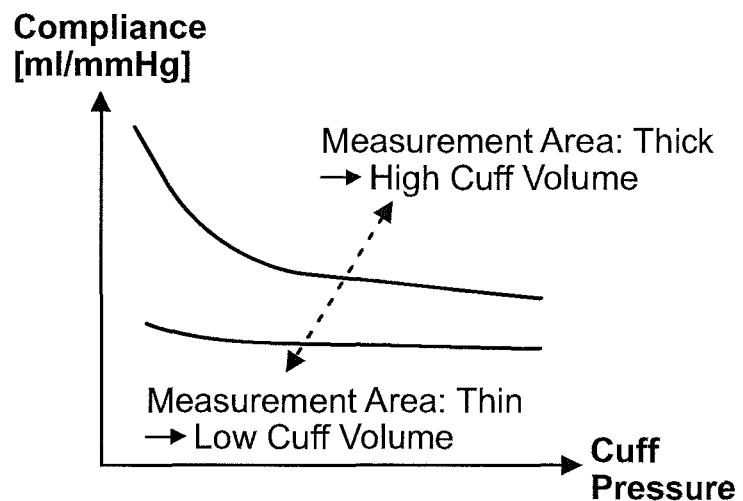
FIG. 5 is a diagram illustrating cuff compliance properties.
FIG. 6 illustrates a table in which correction coefficients are stored according to the first embodiment.

Meanwhile, due to cuff compliance properties illustrated in FIG. 5, the cuff compliance increases the thicker the measurement area is (that is, the longer the circumferential length is), and thus it can be seen that even if the blood vessel volume change is the same, the calculated pulse wave amplitude will differ depending on the thickness of the measurement area. Note that the "cuff compliance" referred to here is the necessary volume for the cuff pressure to change by 1 mmHg, and the unit thereof is ml/mmHg.

Accordingly, it is necessary to determine the pulse wave amplitude, detected when the inflation speed of the cuff 20 is changed, in accordance with a rate of change in the inflation speed and the circumferential length of the measurement area. Here, the rate of change in the inflation speed is determined in accordance with a rate of change in the inflation speed target, and "rate of change" refers to a ratio between the pre-change inflation speed target and the post-change inflation speed target.

A table TB, illustrated in FIG. 6, that holds circumferential lengths L of the measurement area and correction coefficients α that are based on the post-change inflation speed target V, is stored in the memory unit 42. Here, because the pre-change inflation speed target is constant, it can be said that correction coefficients α that correspond to respective sets of circumferential lengths L and rates of change in the inflation speed target are stored in the table TB. Note that the data in FIG. 6 is obtained in advance through experimentation.

The circumferential length L of the measurement area is estimated by the circumferential length estimating unit 401 during blood pressure measurement, based on pressure change properties occurring immediately after the start of inflation. After the inflation speed target has been changed by the target changing unit 114, the correction coefficient determination unit 402 searches the table TB based on the circumferential length L and the post-change inflation speed target V, and reads out the corresponding correction coefficient α. The correction coefficient α is determined in this manner.

The amplitude correction unit 113 extracts a pulse wave with every beat from the pulse wave signal (pressure signal) inputted from the pulse wave detection unit 118. Specifically, the amplitude correction unit 113 calculates a difference between a current value and a preceding value of the pressure as indicated by the pressure signal, determines whether or not the difference exceeds a reference value, and extracts a rising/falling point in the signal based on a result of the determination. The pulse wave (one unit of amplitude) can be extracted as a result.

The amplitude correction unit 113 corrects the amplitude value of the pulse wave using the correction coefficient α. In other words, a detected pulse wave amplitude value Amp is corrected as (Amp×α). The corrected pulse wave is outputted to the blood pressure determination unit 117. The blood pressure determination unit 117 determines the blood pressure through the oscillometric technique using the pulse wave whose amplitude has been corrected.

Figures 7, 8:
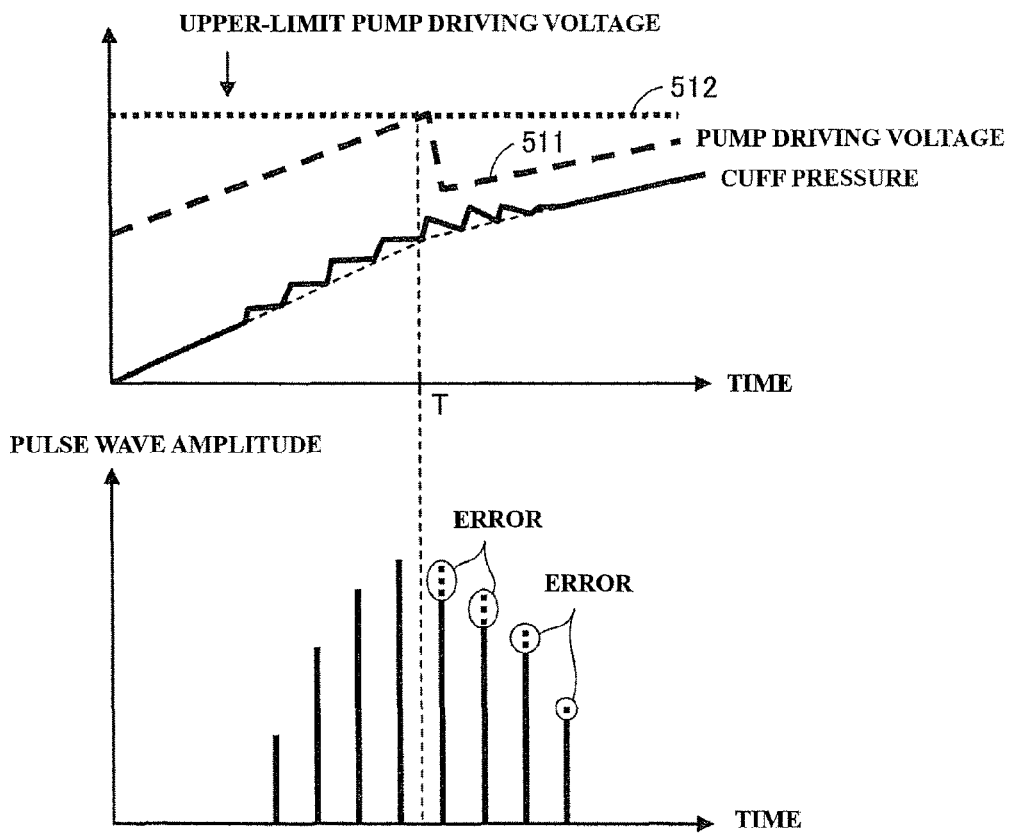
FIG. 7 is a diagram schematically illustrating pulse wave amplitude correction according to the first embodiment.
FIG. 8 illustrates a table referred to in order to estimate a circumferential length according to the first embodiment.

FIG. 7 is a diagram schematically illustrating the pulse wave amplitude correction according to the present embodiment. As shown in FIG. 7, when the inflation speed target is changed to achieve constant speed inflation within a range in which there is an excess margin in the output of the pump 51 as described above, error in the pulse wave amplitude caused by the change can be eliminated through the aforementioned amplitude correction.

Circumferential Length Estimation

Figure 9:
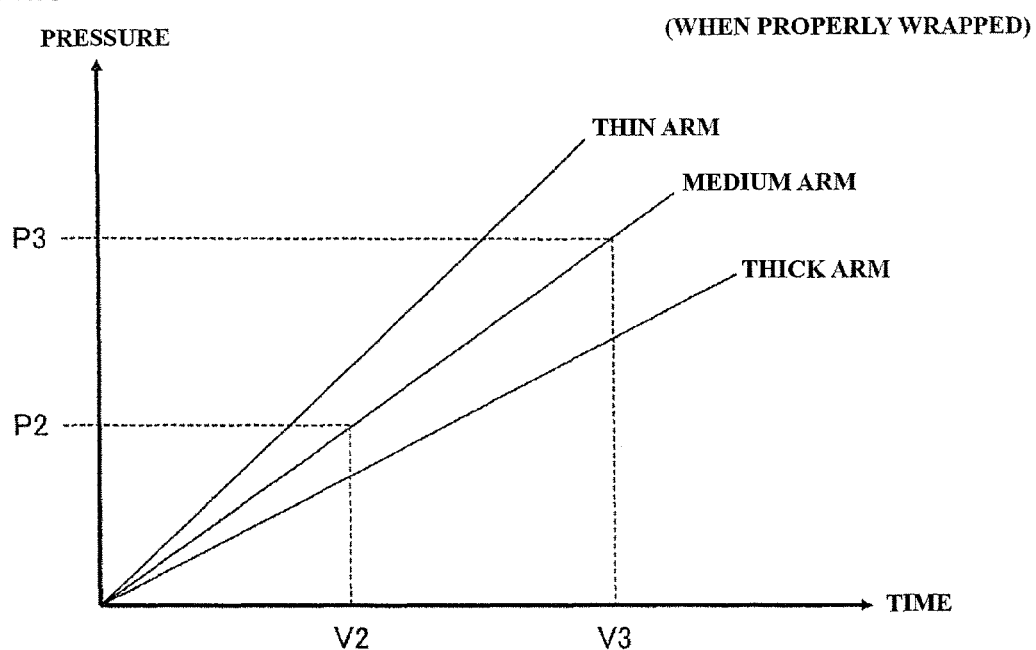
FIG. 9 illustrates a graph showing cuff pressure-inflation time properties (when properly wrapped) according to the first embodiment.

Estimation of the circumferential length of the measurement area according to the present embodiment will be described next. FIG. 8 illustrates an example of a table 433 referred to in order to estimate the circumferential length L of the measurement area according to the present embodiment. The table 433 stores constant speed inflation times required to increase the cuff pressure to a predetermined pressure in the case where the cuff 20 is "properly wrapped" around the measurement area, along with corresponding circumferential lengths L. The data in the table 433 is obtained in advance through experimentation. FIG. 9 illustrates a graph showing cuff pressure-inflation time properties (when properly wrapped) according to the present embodiment. The data shown in FIGS. 8 and 9 indicates values based on data sampled from many measurement subjects using the electronic blood pressure meter 100. Here, "properly wrapped" refers to a state where the circumferential length of the measurement area is essentially the same as the length of the circumference along the inner diameter of the cuff 20 when wrapped on the measurement area (that is, the diameter of a cross-section of an arm, which serves as the measurement area). The present embodiment assumes that the blood pressure is measured during the properly-wrapped state.

Here, it is assumed that the amount of air required for the cuff pressure to move from a pressure P2 to a pressure P3 is a fluid volume $\Delta V23$, based on the cuff pressure in the cuff 20 wrapped around the measurement area and a volume change in the fluid supplied to the cuff 20 (which is air, in the present embodiment) (see FIG. 9). In constant speed inflation (where the RPM of the pump 51 are constant), the inflation time required to supply air equivalent to the fluid volume $\Delta V23$ is a constant time (here, a time V23 from a point in time V2 to a point in time V3). However, the time V23 changes depending on the circumferential length L of the measurement area.

For example, in the case where the cuff 20 is "properly wrapped" around measurement areas having different circumferential lengths, the time V23 decreases as the circumferential length decreases (with thinner arms) and the time V23 increases as the circumferential length increases (with thicker arms), as indicated in FIG. 9.

Using the timer unit 45, the circumferential length estimating unit 401 measures an amount of time required for the cuff pressure to change from 0 mmHg (the pressure P2) to 20 mmHg (the pressure P3), based on the cuff pressure detected after the inflation has started. The corresponding circumferential length L is then obtained by searching the table 433 based on the measured time. The circumferential length L is then supplied to the correction coefficient determination unit 402. The correction coefficient determination unit 402 searches the table TB based on the circumferential length L and the post-change inflation speed target V, and reads out the corresponding correction coefficient $\alpha$. The correction coefficient $\alpha$ is determined in this manner.

Although the circumferential length L is described here as being estimated (measured) during blood pressure measurement, the circumferential length L may be inputted by the measurement subject operating the operation unit 41. Alternatively, circumferential lengths L may be stored in the memory unit 42 in advance on a measurement subject-by-measurement subject basis.

Flowchart

Figure 10:
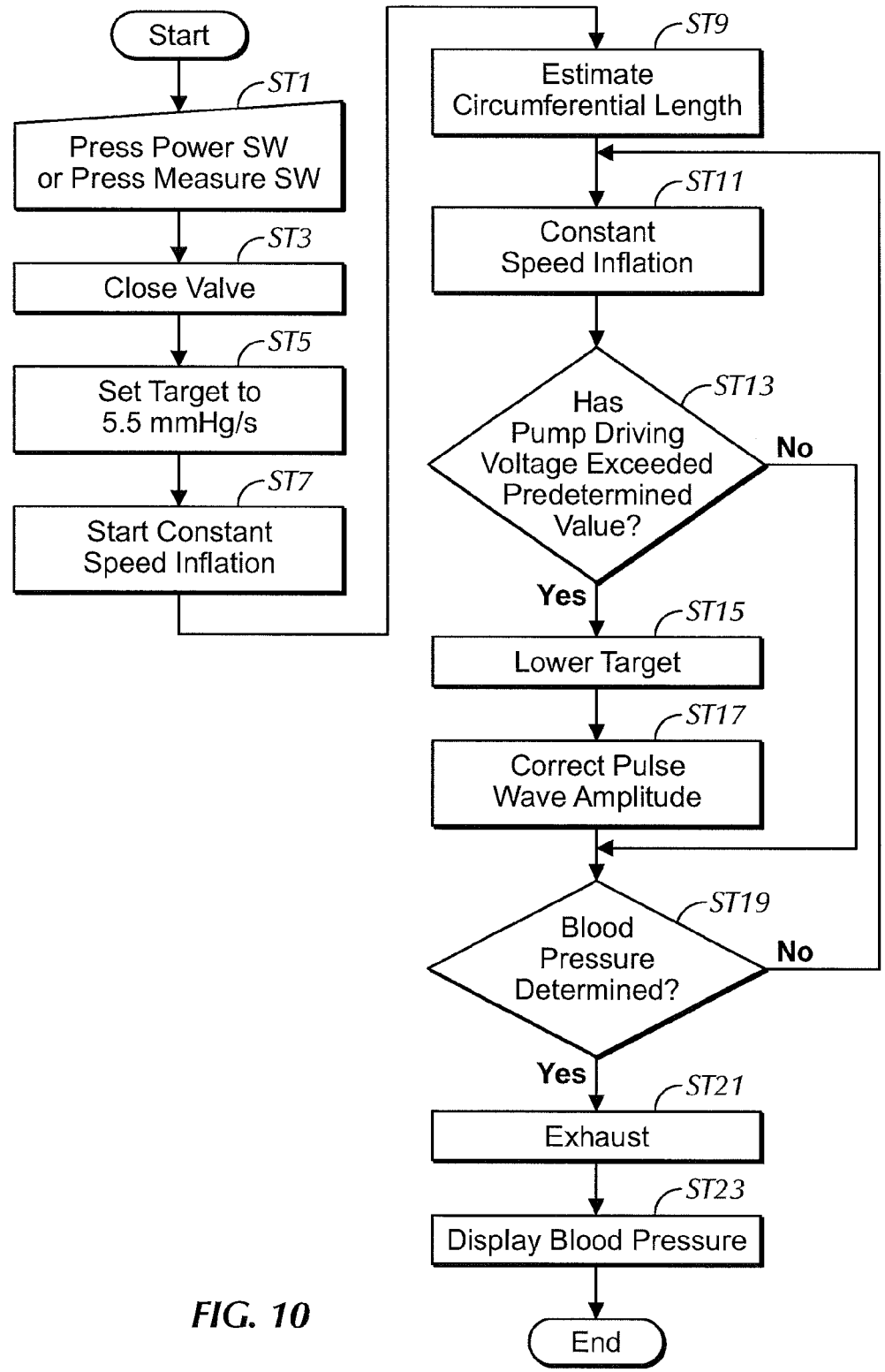
FIG. 10 is a flowchart illustrating a blood pressure measurement process according to the first embodiment.

FIG. 10 is a flowchart illustrating a blood pressure measurement process according to the present embodiment. A program based on this flowchart is stored in the memory unit 42 in advance, and is read out from the memory unit 42 and executed by the CPU 10.

When a measurement subject manipulates the power switch 41A (or the measure switch 41B) while the cuff 20 is "properly wrapped" on the measurement area (step ST1), the CPU 10 executes a predetermined initialization process, after which the CPU 10 outputs a control signal for closing the valve 52 to the valve driving circuit 54. The valve 52 is closed by the valve driving circuit 54 as a result (step ST3). "SW" in FIG. 10 means "switch".

The driving control unit 111 resets the inflation speed target to a predetermined value (for example, 5.5 mmHg/sec) and outputs that value to the inflation control unit 115 (step ST5). The inflation control unit 115 outputs a control signal to the pump driving circuit 53 so that the cuff pressure is increased at a constant speed in accordance with the inflation speed target (5.5 mmHg/sec). Based on the control signal, the pump driving circuit 53 outputs a driving signal (a voltage signal) to the pump 51 so that the cuff pressure is increased at a constant speed corresponding to the inflation speed target. The constant speed increase of the cuff pressure begins as a result (step ST7).

After the constant speed inflation has started, the circumferential length estimating unit 401 estimates the circumferential length L of the measurement area according to the aforementioned procedure (step ST9). The cuff pressure continues to increase at the constant speed during the estimation as well (step ST11).

The constant speed inflation is carried out by performing feedback control on the driving signal for the pump 51, as described earlier. In the feedback control process, the target changing unit 114 is consecutively inputted with the driving voltage 511 for the pump 51, compares the voltage value of the driving voltage 511 with a predetermined voltage value (for example, the upper-limit driving voltage 512 of the pump 51) stored in the memory unit 42, and based on a result of the comparison, determines whether or not the condition (value of driving voltage 511>predetermined voltage value) is met (step ST13).

If it is determined that the condition is not met (NO in step ST13), the process advances to step ST19.

During the process of the constant speed inflation, the blood pressure determination unit 117 determines the blood pressure through the oscillometric method based on the pulse wave amplitude inputted from the amplitude correction unit 113 and the cuff pressure detected by the pressure detection unit 112. The blood pressure cannot be determined before sufficient inflation has been achieved (NO in step ST19), and thus the process returns to step ST11, the processes that follow thereafter are repeated, and the constant speed inflation continues.

However, when the inflation is sufficient and the blood pressure is determined (YES in step ST19), the deflation control unit 116 outputs a control signal to stop the pump 51 and open the valve 52. As a result, the air is exhausted from the air bladder 21 and the cuff pressure decreases (step ST21). When the deflation control unit 116 has determined that the exhausting is complete based on the cuff pressure outputted from the pressure detection unit 112, the display control unit 120 displays the blood pressure and pulse frequency determined by the blood pressure determination unit 117 in the display unit 40 (step ST23). In addition, the determined blood pressure and pulse frequency are stored in the memory unit 42 along with the measurement time measured by the timer unit 45.

Returning to step ST13, when the target changing unit 114 determines that the condition (value of the driving voltage 511>predetermined voltage value) is met (YES in step ST13), or in other words, that the output capability of the pump 51 has approached its upper limit (see a time T in FIG. 7), the inflation speed target is reduced to a predetermined value (for example, 3.0 mmHg/sec) (step ST15). The constant speed inflation through feedback control is continued using the post-change inflation speed target. In this manner, the constant speed inflation control is executed within a range in which there is an excess margin in the output of the pump 51. The inflation speed target may be changed a plurality of times, or the measurement may be stopped and an error displayed when the inflation speed has dropped below a lower limit value.

When the inflation speed target is changed, the correction coefficient determination unit 402 searches the table TB based on the post-change inflation speed target and the circumferential length L estimated in step ST9 and reads out the corresponding correction coefficient $\alpha$. The pulse wave amplitude is corrected using the read-out correction coefficient α, and the corrected pulse wave amplitude is outputted to the blood pressure determination unit 117 (step ST17). Through this, the blood pressure determination unit 117 determines the blood pressure using the corrected pulse wave amplitude and the cuff pressure. Thereafter, the processes of step ST19 and on are repeated in the same manner as described above.

According to the present embodiment, the pulse wave amplitude is corrected to eliminate error therein caused by a change in a constant inflation speed resulting from a change in the inflation speed target, and the blood pressure is determined using the corrected pulse wave amplitude; accordingly, an accurate blood pressure measurement can be carried out.

Second Embodiment

In the aforementioned first embodiment, the timing at which the inflation speed target is changed is determined based on the driving voltage 511 of the pump 51; however, in the present second embodiment, the timing at which the inflation speed target is changed may be determined depending on the blood pressure level. In other words, because the cuff pressure at which the pulse wave is detected after the inflation is started differs depending on the blood pressure level, the timing at which the inflation speed target is changed may be varied based on differences in the cuff pressure at which the pulse wave is detected.

Note that the inflation speed is controlled to a constant speed within a range where a condition (driving voltage 511≦upper-limit driving voltage 512) is met, or in other words, within a range in which there is an excess margin in the output of the pump 51, in the present embodiment as well.

Figure 11A:
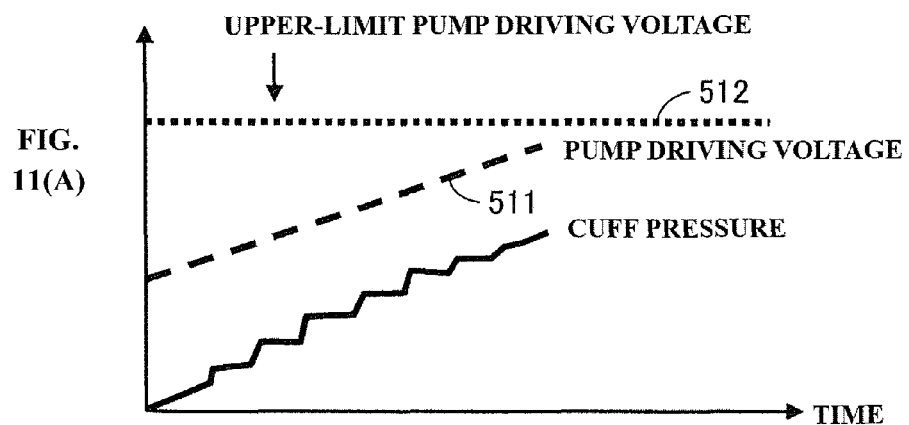
FIGS. 11(A) and 11(B) are diagrams illustrating a timing at which a pulse wave is detected during a process of inflation according to a second embodiment.
Figure 11B:
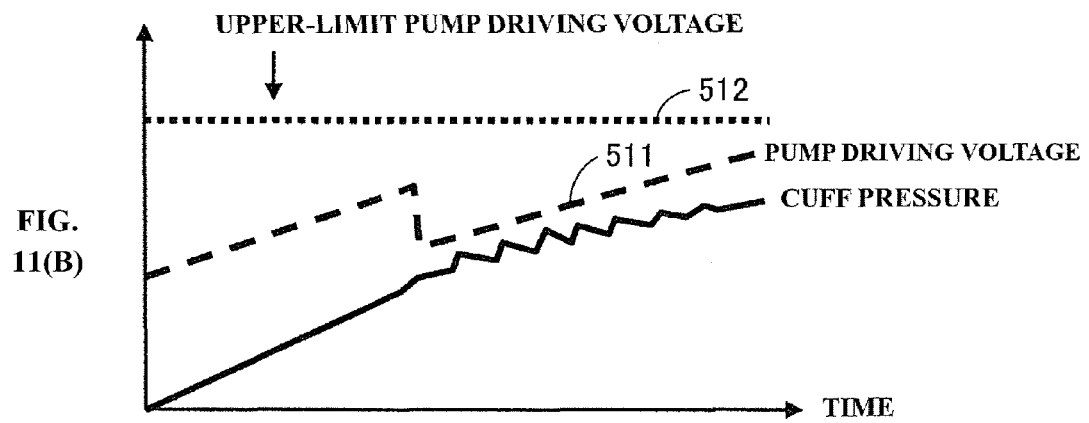

FIGS. 11(A) and 11(B) are diagrams illustrating a timing at which a pulse wave is detected during a process of inflation according to the second embodiment. FIGS. 11(A) and 11(B) illustrate a change in the driving voltage 511 over time during the process of inflation and a change in the cuff pressure on which the pulse wave is superimposed.

As shown in FIG. 11(A), in the case of a measurement subject having a comparatively low blood pressure, the pulse wave appears in a low cuff pressure range during the process of constant speed inflation, and thus there are cases where the blood pressure measurement can be completed without changing the inflation speed target.

On the other hand, as shown in FIG. 7, in the case of a measurement subject having a comparatively high blood pressure, it is necessary to change the inflation speed target within the range of the cuff pressure where the pulse wave appears, and it is thus necessary to correct the pulse wave amplitude. Accordingly, in the case where the blood pressure of the measurement subject is high and it is thought that it will be necessary to change the inflation speed target within the range of the cuff pressure where the pulse wave appears, the measurement is started at a low inflation speed target, as illustrated in FIG. 11B; accordingly, the blood pressure can be determined through constant speed inflation without changing the inflation speed target, or in other words, without correcting the pulse wave amplitude.

Figure 12:
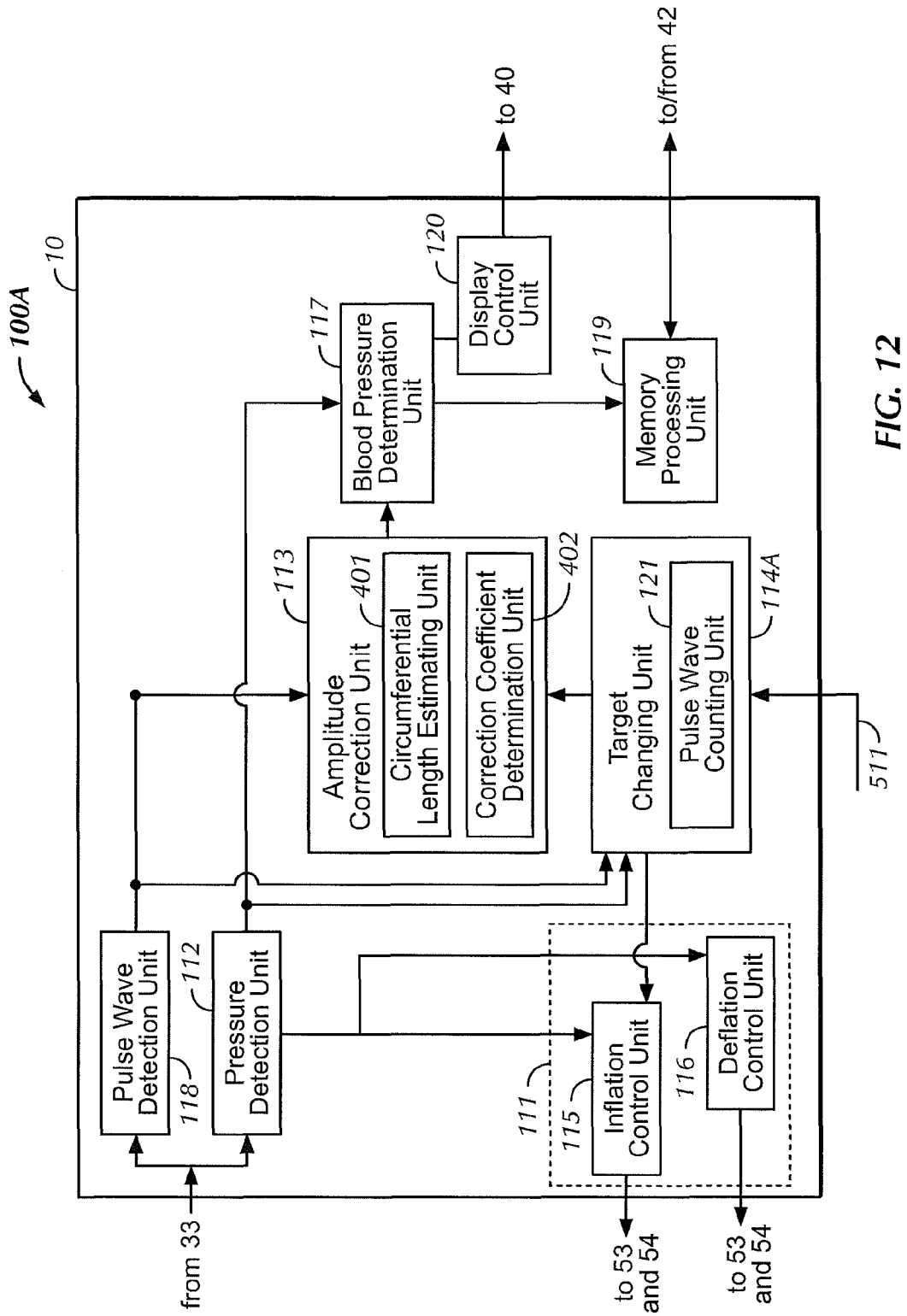
FIG. 12 is a functional block diagram illustrating the functional configuration of an electronic blood pressure meter according to the second embodiment.

FIG. 12 is a functional block diagram illustrating the functional configuration of an electronic blood pressure meter 100A according to the present embodiment. The functional configuration illustrates the functions provided by the CPU 10 as well as related peripheral units.

The electronic blood pressure meter 100A illustrated in FIG. 12 differs from the functional configuration illustrated in FIG. 2 in that a target changing unit 114A is provided instead of the target changing unit 114. The cuff pressure detected by the pressure detection unit 112 is inputted into the target changing unit 114A. In addition, the target changing unit 114A includes a pulse wave counting unit 121 that counts the number of pulse waves outputted by the pulse wave detection unit 118, and the inflation speed target is changed based on a counted value.

Figure 13:
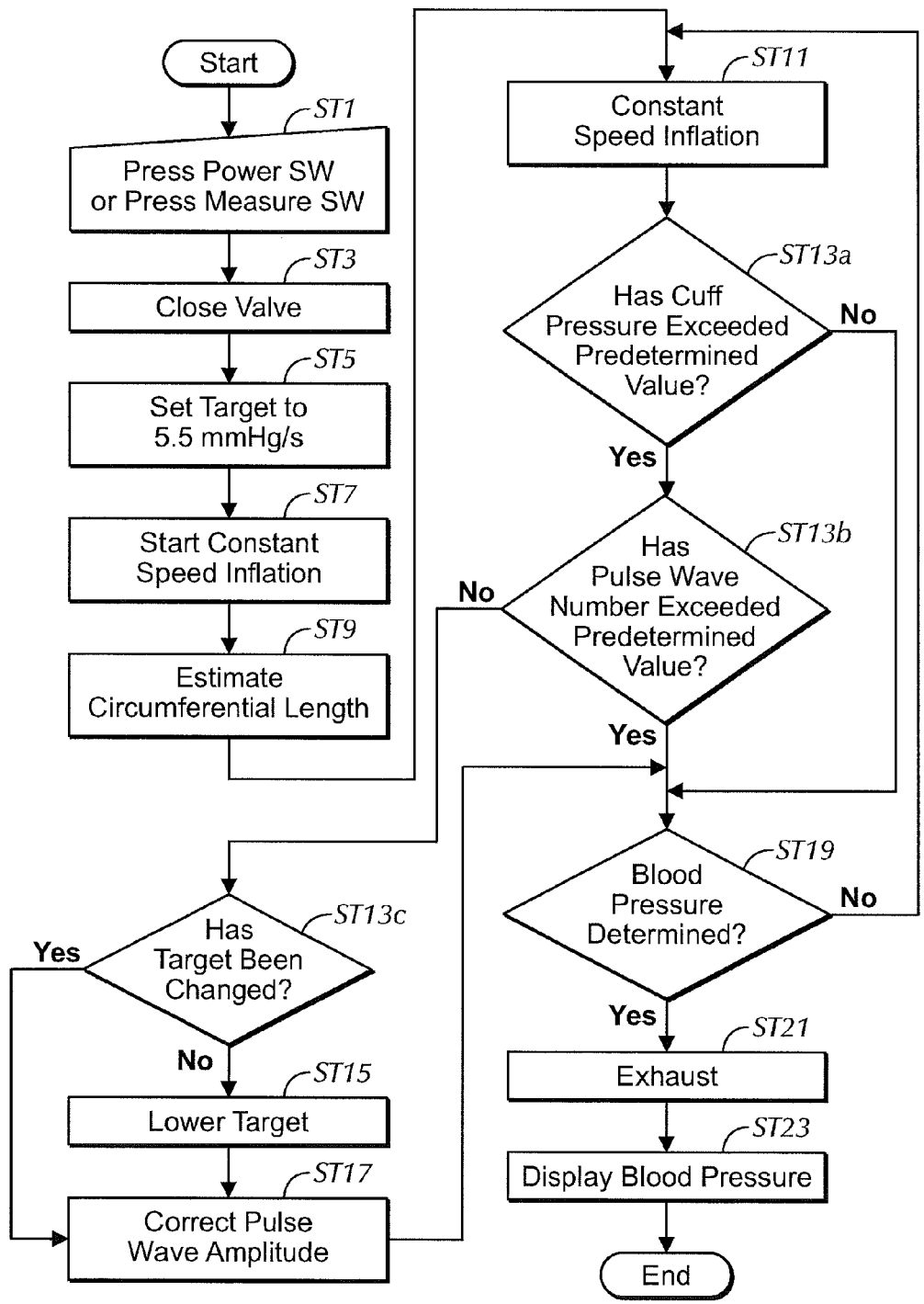
FIG. 13 is a flowchart illustrating a blood pressure measurement process according to the second embodiment.

FIG. 13 is a flowchart illustrating a blood pressure measurement process according to the present embodiment. A program based on this flowchart is stored in the memory unit 42 in advance, and is read out from the memory unit 42 and executed by the CPU 10. A blood pressure measurement process according to the present embodiment will be described with reference to the flowchart in FIG. 13.

First, in steps ST1 to ST11, the same processes as those illustrated in FIG. 10 are carried out.

Thereafter, the target changing unit 114A compares the cuff pressure detected by the pressure detection unit 112 with a predetermined value (for example, 50 mmHg) and determines whether or not the cuff pressure is greater than the predetermined value based on a result of the comparison (step ST13a). If it is determined that the cuff pressure is less than or equal to the predetermined value (NO in step S13a), the process advances to step ST19. However, if it is determined that the cuff pressure is greater than the predetermined value (YES in step ST13a), a blood pressure level screening is executed (step ST13b).

Specifically, the pulse wave counting unit 121 counts the pulse waves detected from the start of the inflation, and the target changing unit 114A compares the counted value with a predetermined value (for example, two beats) and determines whether or not the counted value is greater than the predetermined value based on a result of the comparison (step ST13b).

If it is determined that the number of detected pulse waves is less than or equal to the predetermined value (NO in step ST13b), it is assumed that the measurement subject has a high blood pressure, and the target changing unit 114A changes the inflation speed target (NO in step ST13c; step ST15). For example, the inflation speed target is reduced to a predetermined value (for example, 3.0 mmHg/sec) (step ST15), and the constant speed inflation is executed using the post-change inflation speed target. Through this, constant speed inflation control is executed within a range in which there is an excess margin in the output of the pump 51.

As a result of the inflation speed target being changed (YES in step ST13c), the pulse wave amplitude is corrected by the amplitude correction unit 113 in the same manner as described before, after which the blood pressure determination unit 117 executes the process for determining the blood pressure using the corrected pulse wave amplitude (step ST17). Thereafter, the same processes as described before (step ST19 to step ST23) are carried out.

Returning to step ST13a and step ST13b, the constant speed inflation is continued without changing the inflation speed target while it is determined that the counted value for the pulse wave is less than or equal to the predetermined value during the period where the cuff pressure is less than the predetermined pressure (YES in step ST13a; YES in step ST13b).

Note that rather than executing the blood pressure level screening, the measurement subject may instead input information indicating his or her blood pressure level in advance using the operation unit 41. Alternatively, a blood pressure of the measurement subject measured in the past may be read out from the memory unit 42, and the blood pressure level may be determined based on a result of comparing that blood pressure level with a standard blood pressure.

Furthermore, although the number of pulse waves detected in a range from when the inflation is started to when the cuff pressure reaches 50 mmHg is counted, the predetermined range of the cuff pressure in which the counting is to take place is not limited to this range.

According to the present embodiment, the blood pressure level of the measurement subject is estimated based on the number of pulse waves detected in a comparatively early period following the start of inflation, and the inflation speed target is changed based on a result of the estimation. Accordingly, in the case of a measurement subject having a comparatively high blood pressure, the inflation speed target is changed to a low value in the comparatively early period following the start of inflation, and the constant speed inflation is then carried out; as a result, the blood pressure can be determined without changing the inflation speed target thereafter, or in other words, without correcting the pulse wave amplitude.

Third Embodiment

In the aforementioned first and second embodiments, the post-change inflation speed target is described as a fixed predetermined value (for example, 3.0 mmHg/sec); however, in the present third embodiment, the value may be varied based on the circumferential length L. In other words, because the volume of the cuff 20 that is wrapped around the measurement area increases as the circumferential length L of the measurement area increases, a higher output (a greater discharge amount) is demanded from the pump 51. Accordingly, it is desirable to determine the inflation speed target based on the circumferential length L in order to inflate the cuff 20 quickly.

Note that the inflation speed is controlled to a constant speed within a range where a condition (driving voltage 511≦upper-limit driving voltage 512) is met, or in other words, within a range in which there is excess margin in the output of the pump 51, in the present embodiment as well.

Figure 14:
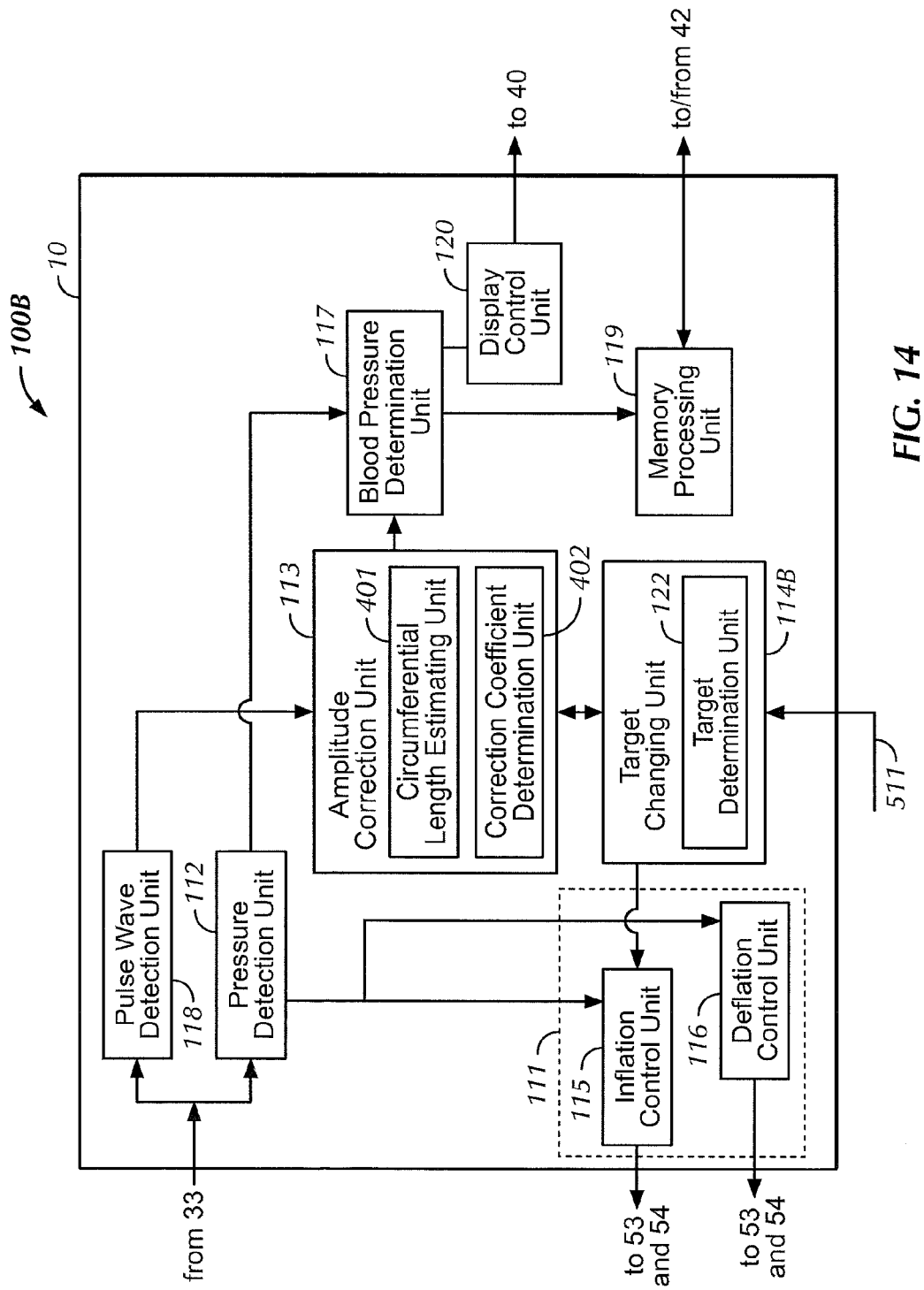
FIG. 14 is a functional block diagram illustrating the functional configuration of an electronic blood pressure meter according to the third embodiment.

FIG. 14 is a functional block diagram illustrating the functional configuration of an electronic blood pressure meter 100B according to the present third embodiment. The functional configuration illustrates the functions provided by the CPU 10 as well as related peripheral units.

FIG. 15 illustrates a table TB1 for determining the inflation speed target according to the present embodiment. The electronic blood pressure meter 100B illustrated in FIG. 14 differs from the functional configuration illustrated in FIG. 2 in that a target changing unit 114B is provided instead of the target changing unit 114. The target changing unit 114B includes a target determination unit 122 that takes the circumferential length L estimated by the circumferential length estimating unit 401 as an input, searches the table TB1 shown in FIG. 15 based on the circumferential length L, and determines the post-change inflation speed target.

The table TB1 is stored in the memory unit 42 in advance. In the case where the inflation speed target is changed during the process of inflation, the target determination unit 122 searches the table TB1 based on the estimated circumferential length L and reads out an inflation speed v. The target changing unit 114B sets the read-out inflation speed v as the post-change inflation speed target.

Note that the target changing unit 114A of the electronic blood pressure meter 100A illustrated in FIG. 12 may include this target determination unit 122.

Accordingly, the inflation speed target can be set in accordance with the circumferential length L of the measurement area, after which the constant speed inflation can be carried out.

Fourth Embodiment

In the aforementioned embodiments, it is assumed that the inflation speed, which corresponds to an amount of air supplied from the pump 51 to the cuff 20 per unit of time (a discharge flow rate), is proportional to the voltage applied to the pump 51 by the pump driving circuit 53, and the timing at which the inflation speed target is changed is determined based on the driving voltage 511 of the pump 51.

However, the method for determining the timing is not limited thereto, and in the case where the power source 44 is a battery, the timing at which the inflation speed target is changed may be determined based on an inter-terminal voltage of the battery (called a "cell voltage" hereinafter). In other words, in the electronic blood pressure meter, the pump is a component that consumes a large amount of energy during blood pressure measurement, and thus the inflation speed of the pump can be considered to be proportional to the cell voltage.

Note that the aforementioned function for correcting the amplitude in accordance with the change in the inflation speed target can be applied in the following embodiments as well.

Figure 16:
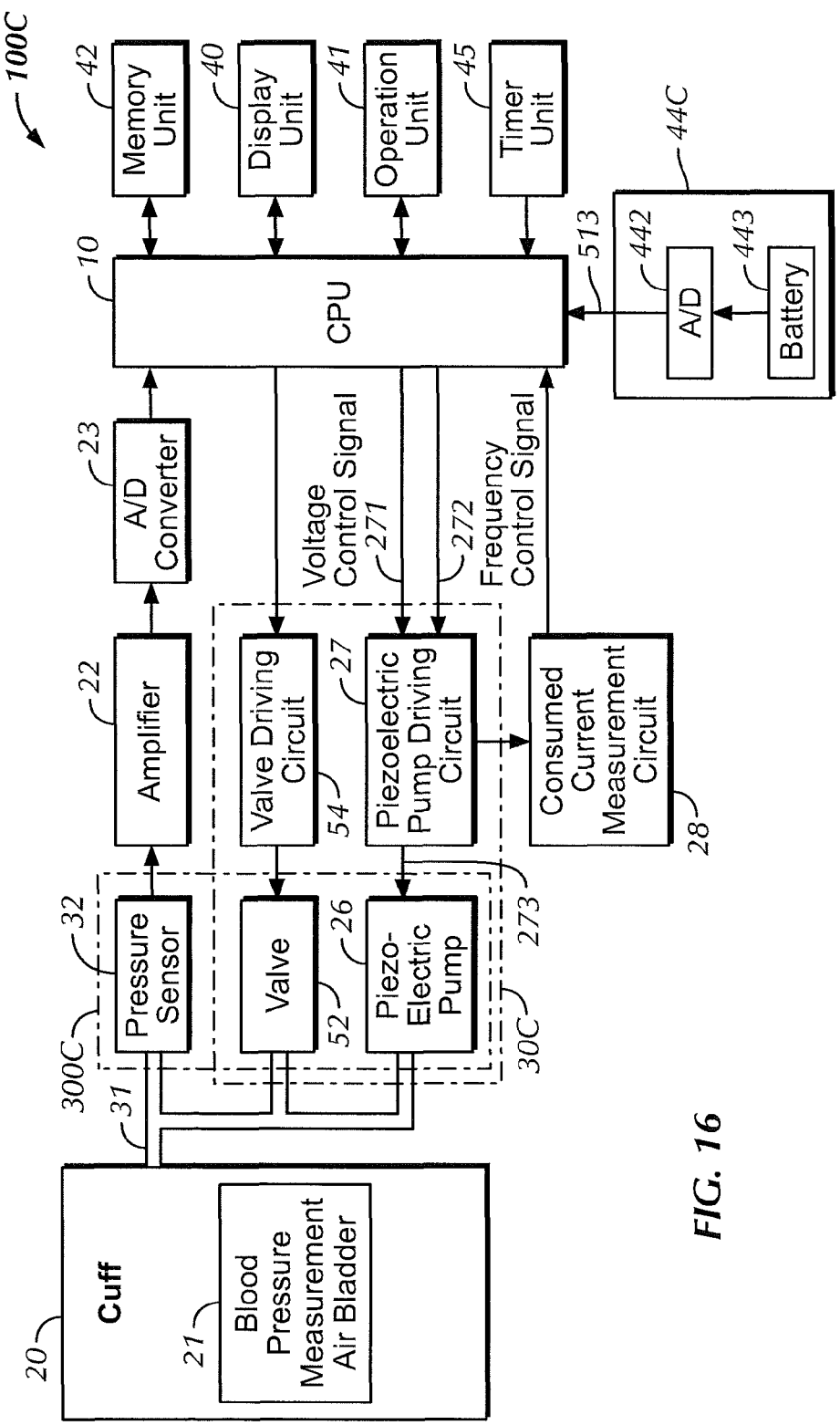
FIG. 16 is a block diagram illustrating the hardware configuration of an electronic blood pressure meter according to a fourth embodiment.
Figure 17:
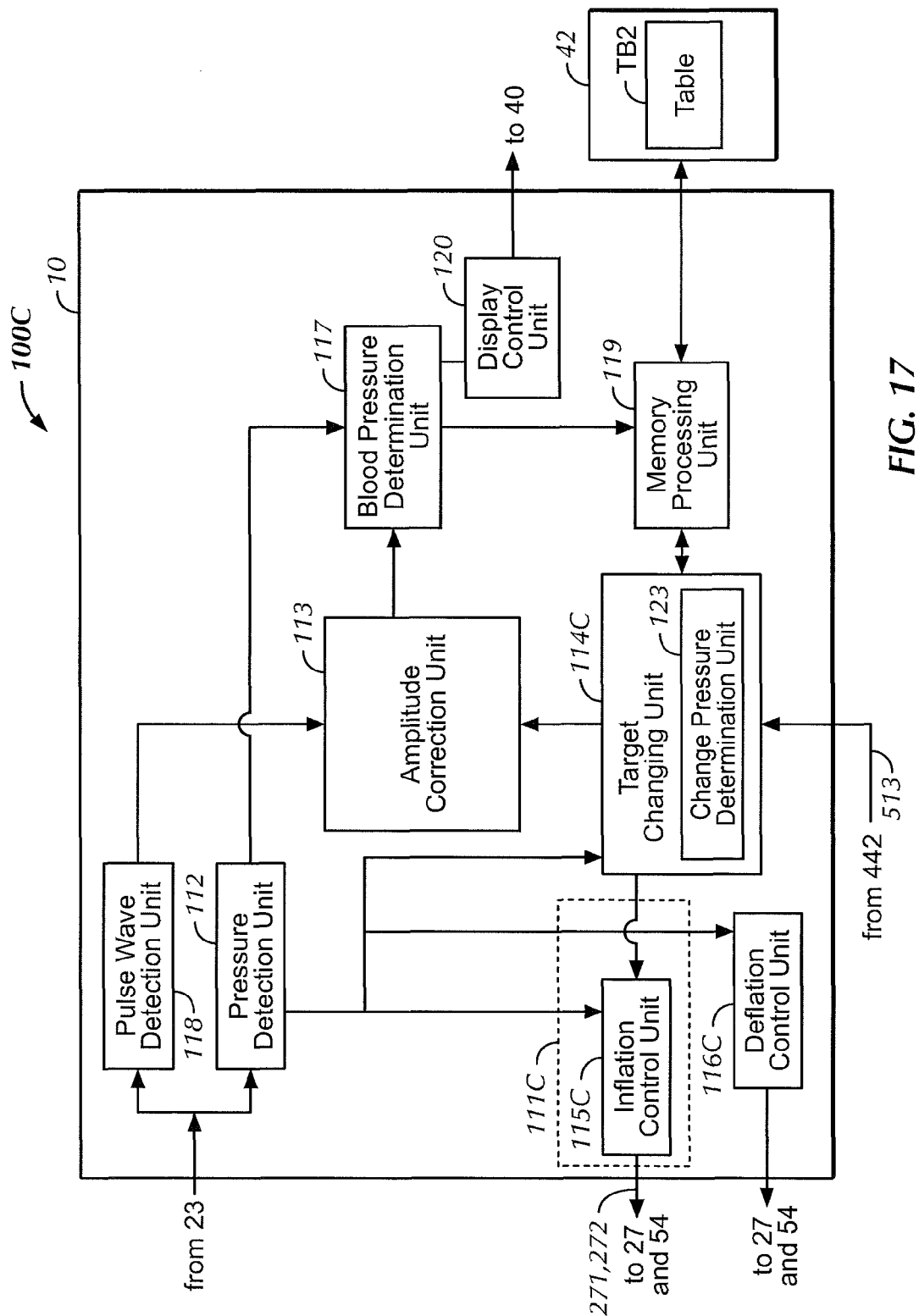
FIG. 17 is a block diagram illustrating the functional configuration of the electronic blood pressure meter according to the fourth embodiment.

FIG. 16 is a block diagram illustrating the hardware configuration of an electronic blood pressure meter 100C according to the present fourth embodiment, and FIG. 17 is a block diagram illustrating the functional configuration of the electronic blood pressure meter 100C according to the fourth embodiment.

As shown in FIG. 16, the electronic blood pressure meter 100C has the same basic configuration as that shown in FIG. 1, but differs therefrom in that an air system 300C is provided instead of the air system 300, an adjustment unit 30C is provided instead of the adjustment unit 30, a power source 44C is provided instead of the power source 44, and a consumed current measurement circuit 28 is added. Accordingly, the differences will be described below.

The air system 300C includes a piezoelectric pump 26 instead of the pump 51, but otherwise has the same configuration as the air system 300. Likewise, the adjustment unit 30C includes the piezoelectric pump 26 and a piezoelectric pump driving circuit 27 instead of the pump 51 and the pump driving circuit 53, but otherwise has the same configuration as the adjustment unit 30.

The piezoelectric pump 26 is a micro pump that uses a piezoelectric element as its driving source. The piezoelectric pump 26 includes a piezoelectric actuator driven by a vibration control voltage signal 273, a diaphragm that is layered thereupon, and a pump chamber that contracts and expands in response to the diaphragm displacing, or in other words, in response to vibrations; air is supplied to the cuff 20 via the pump chamber that contracts and expands.

The piezoelectric pump driving circuit 27 generates and outputs the vibration control voltage signal 273 based on a voltage control signal 271 and a frequency control signal 272 from the CPU 10. The frequency control signal 272 matches a resonance frequency determined by the dimensions of the piezoelectric actuator and the diaphragm layered thereupon, and data indicating the resonance frequency is stored in the memory unit 42 in advance. Meanwhile, the voltage control signal 271 indicates a voltage value determined based on the inflation speed target undergoing feedback control as described above. The piezoelectric pump driving circuit 27 generates the vibration control voltage signal 273, which is an AC voltage signal near the resonance frequency, based on the voltage control signal 271 and the frequency control signal 272, and applies the vibration control voltage signal 273 to the piezoelectric actuator.

The consumed current measurement circuit 28 measures the current consumed at the piezoelectric pump driving circuit 27 using a current sensor or the like, and outputs the measured value to the CPU 10 as a consumed current value. In the electronic blood pressure meter 100C, the components aside from the piezoelectric pump driving circuit 27 consume a small current, and thus the current consumed by the piezoelectric pump driving circuit 27 can be considered equal to the current consumed by the electronic blood pressure meter 100C during operation.

The power source 44C includes a removable battery 443 and an A/D (analog/digital) converter 442 that takes a cell voltage of the battery 443 as an input, converts that voltage into digital data, and outputs voltage data 513 indicating a cell voltage value to the CPU 10. A non-chargeable primary battery such as a dry cell battery, or a chargeable secondary battery, can be employed as the battery 443.

The pressure sensor 32 is a electrostatic capacitance-type pressure sensor, and a capacity value thereof changes based on the cuff pressure. The pressure sensor 32 outputs a signal based on the cuff pressure to an amplifier 22. The amplifier 22 amplifies the signal inputted from the pressure sensor 32 and outputs the amplified signal to an A/D (analog/digital) converter 23. The A/D converter 23 converts the amplified signal inputted from the amplifier 22 (an analog signal) into a digital signal and outputs the post-conversion digital signal to the CPU 10. Through this, the CPU 10 detects the cuff pressure and the pulse wave.

Functional Configuration

As shown in FIG. 17, the electronic blood pressure meter 100C has the same basic configuration as that shown in FIG. 2, but differs therefrom in that a driving control unit 111C having an inflation control unit 115C that outputs the voltage control signal 271 and the frequency control signal 272 is provided instead of the driving control unit 111 that has the inflation control unit 115, a deflation control unit 116C is provided instead of the deflation control unit 116, a target changing unit 114C that changes the inflation speed target using the voltage data 513 is provided instead of the target changing unit 114, and a table TB2 that is referred to in order to change the inflation speed target is stored in the memory unit 42. Accordingly, only the differences will be described below.

The target changing unit 114C is inputted with the cuff pressure from the pressure detection unit 112 during blood pressure measurement, and changes the inflation speed target at the point in time when a cuff pressure at which the inflation speed target is to be changed has been detected. Here, the cuff pressure at which the inflation speed target is to be changed will be called a "change start pressure". The target changing unit 114C includes a change pressure determination unit 123 in order to determine the change start pressure.

Processing Flowchart

Figure 18:
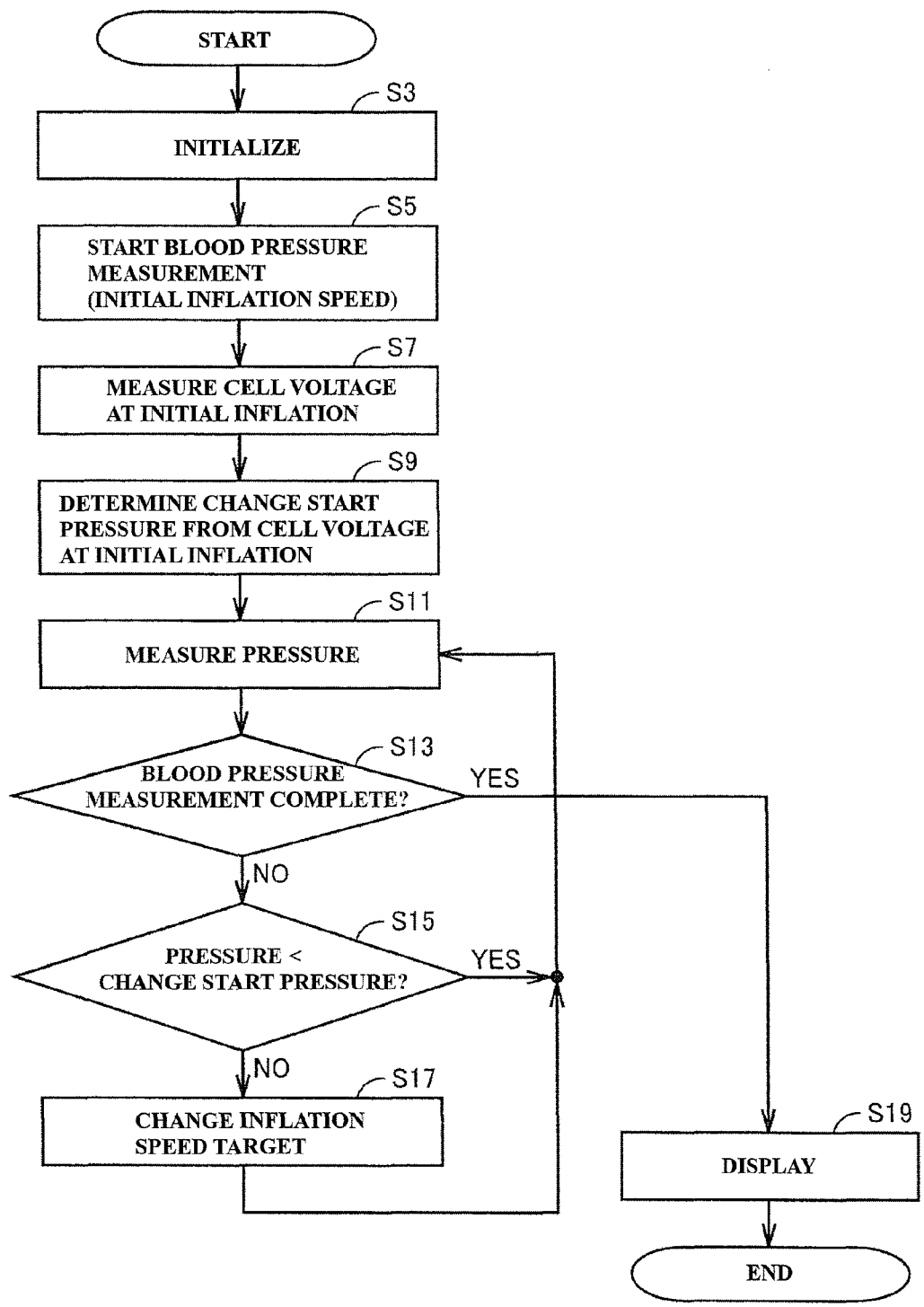
FIG. 18 is a flowchart illustrating a blood pressure measurement process according to the fourth embodiment.

FIG. 18 is a flowchart illustrating a blood pressure measurement process according to the present fourth embodiment. A program based on this flowchart is stored in the memory unit 42 in advance, and is read out from the memory unit 42 and executed by the CPU 10.

When a measurement subject manipulates the power switch 41A (or the measure switch 41B) while the cuff 20 is "properly wrapped" on the measurement area, the CPU 10 executes a predetermined initialization process, after which the CPU 10 outputs a control signal for closing the valve 52 to the valve driving circuit 54. The valve 52 is closed by the valve driving circuit 54 as a result.

Meanwhile, the inflation control unit 115C sets a predetermined (minimum) voltage value for the voltage control signal 271, and sets the aforementioned resonance frequency for the frequency control signal 272 (step S3).

The driving control unit 111C resets the inflation speed target to a predetermined value (for example, 5.5 mmHg/sec) and outputs that value to the inflation control unit 115. The inflation control unit 115 calculates a voltage value from the initial inflation speed target (5.5 mmHg/sec) in accordance with a predetermined conversion formula, generates the voltage control signal 271 based on the calculated voltage value so that the cuff pressure is increased at a constant speed, and outputs the voltage control signal 271 and the frequency control signal 272 to the piezoelectric pump driving circuit 27. The piezoelectric pump driving circuit 27 generates the vibration control voltage signal 273 based on the voltage control signal 271 and the frequency control signal 272, and outputs the vibration control voltage signal 273 to the piezoelectric pump 26. Through this, the piezoelectric pump 26 is driven so that the cuff pressure undergoes a constant speed increase at the inflation speed target (step S5), and the cuff pressure begins to increase at a constant speed as a result.

After the constant speed increase has started, the change pressure determination unit 123 takes the voltage data 513 as an input (step S7), searches the table TB2 in the memory unit 42 based on the voltage data 513, and determines the change start pressure based on a result of the search (step S9).

Figure 19:
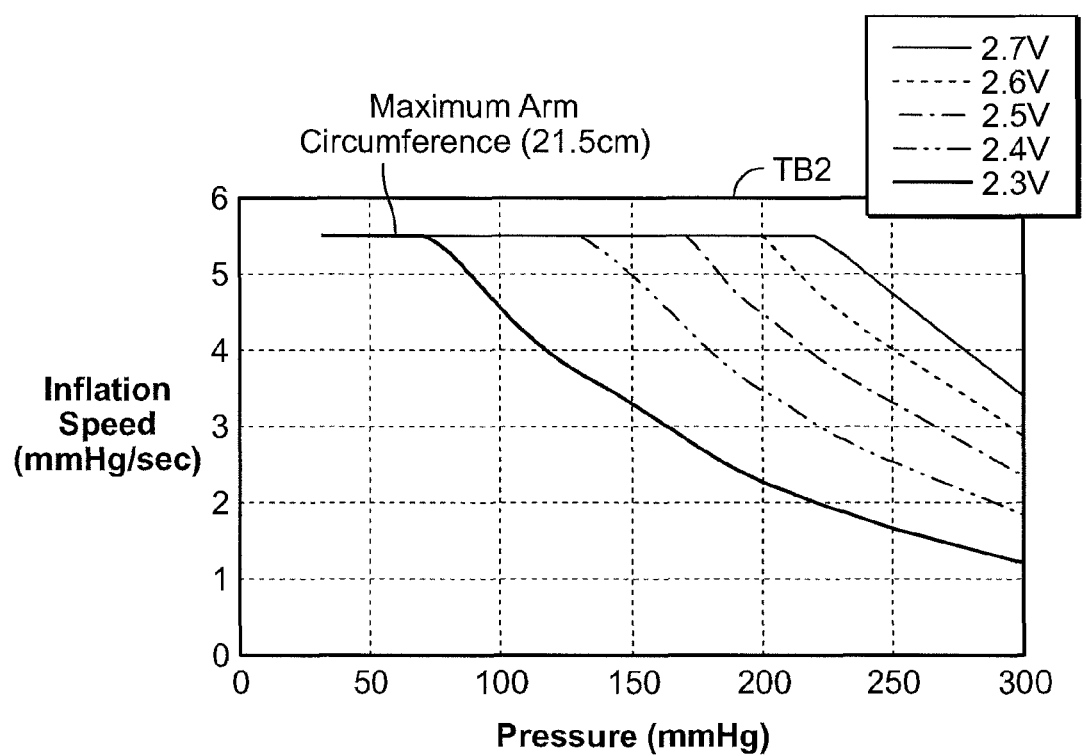
FIG. 19 is a diagram schematically illustrating the content of a table according to the fourth embodiment.

The table TB2 will be described next. Referring to FIG. 19, cuff pressures (mmHg) detected at a timing when the inflation speed begins to decrease (change) from the initial inflation speed in the case where the cuff pressure has undergone a constant speed increase at the initial inflation speed (5.5 mmHg/sec) are associated with each piece of voltage data 513 specifying a cell voltage measured in advance in step S7 and stored in the table TB2. This data is obtained in advance through experimentation and stored in the table TB2. FIG. 19 illustrates an example of a case where the circumference of an arm, serving as the measurement area, is 21.5 cm, which is a maximum value in the experimental data. It can be seen here that a lower change start pressure is set as the cell voltage specified by the voltage data 513 decreases.

For the sake of simplicity, the descriptions of the present embodiment assume that the circumferential length of the measurement subject's arm is the maximum arm circumference indicated in FIG. 19.

When the change start pressure is determined in step S9, the cuff pressure and the pulse wave amplitude are detected while continuing the constant speed inflation, and the blood pressure determination unit 117 carries out a process for determining the blood pressure through the oscillometric method (step S11). When it is determined that the blood pressure has been determined (YES in step S13), the result of the measurement is displayed in the display unit 40 by the display control unit 120 (step S19) and is stored by the memory processing unit 119 in the memory unit 42, in association with a time measured by the timer unit 45. Thereafter, the air is exhausted from the cuff 20 and the measurement process ends.

On the other hand, when it is determined that the blood pressure determination unit 117 has not determined a blood pressure (NO in step S13), the change pressure determination unit 123 compares the cuff pressure from the pressure detection unit 112 with the change start pressure obtained in step S9, and determines whether or not a condition (cuff pressure<change start pressure) is met based on a result of the comparison (step S15). While it is determined that the condition is met (YES in step S15), the process returns to step S11, the same processing is carried out thereafter, and the constant speed inflation is continued at the present inflation speed target.

On the other hand, when it is determined that the aforementioned condition is not met (NO in step S15), the target changing unit 114C decreases the current inflation speed target by a predetermined speed (step S17). The target changing unit 114C calculates a voltage value in accordance with the post-change inflation speed target through a predetermined conversion formula, and outputs a voltage signal indicating the calculated voltage value to the inflation control unit 115C.

The inflation control unit 115C generates the voltage control signal 271 based on the inputted voltage signal and outputs the generated voltage control signal 271 and the frequency control signal 272 to the piezoelectric pump driving circuit 27, and the piezoelectric pump driving circuit 27 generates the vibration control voltage signal 273 based on the voltage control signal 271 and the frequency control signal 272 and outputs the vibration control voltage signal 273 to the piezoelectric pump 26. The cuff pressure begins to increase at a constant speed in accordance with the post-change inflation speed target as a result (step S11).

Note that in step S17, it is assumed that the inflation speed target is changed so as not to drop below a minimum speed (for example, 2.2 mmHg/sec).

Figure 34:
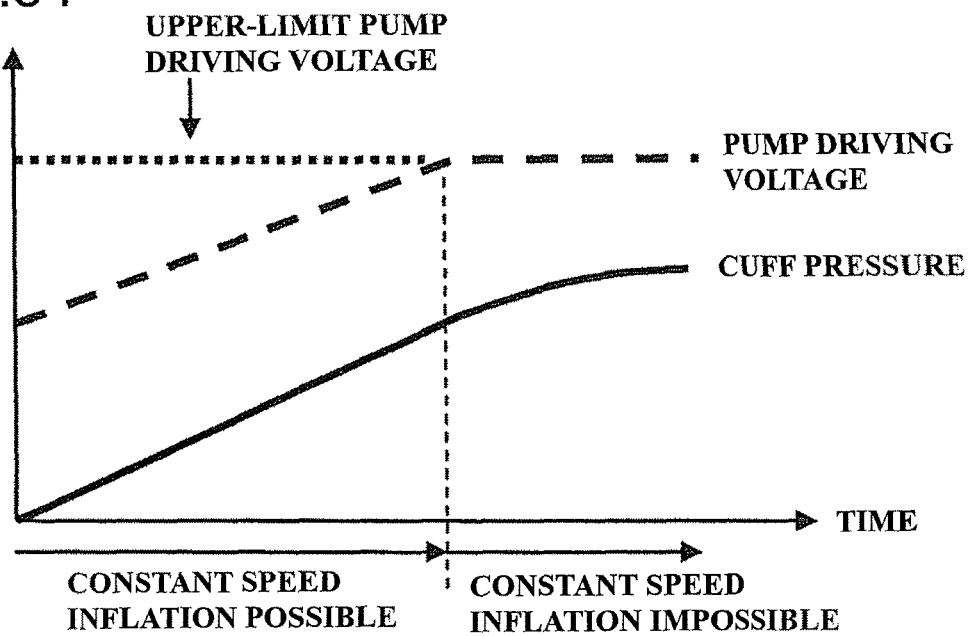
FIG. 34 schematically illustrates a relationship between a constant speed increase in the cuff pressure and a pump driving voltage in a conventional blood pressure meter.

In this manner, according to the present embodiment, based on the cell voltage when the blood pressure measurement starts, the change start pressure is set to be lower as the cell voltage decreases. Accordingly, it is possible to continue constant speed inflation while avoiding a situation where, in the case where the driving voltage undergoing feedback control has exceeded an upper limit voltage for driving the pump, the speed cannot be increased any more and the cuff pressure cannot be increased at a constant speed as a result (see FIG. 34).

Fifth Embodiment

In the fourth embodiment, the timing at which the inflation speed target is changed is determined based on a cell voltage measured at the start of the blood pressure measurement; however, the inflation speed target may be lowered (changed) when the cell voltage measured during the blood pressure measurement has dropped below a constant value (for example, 1.9 V), as will be described in the present embodiment.

Figure 20:
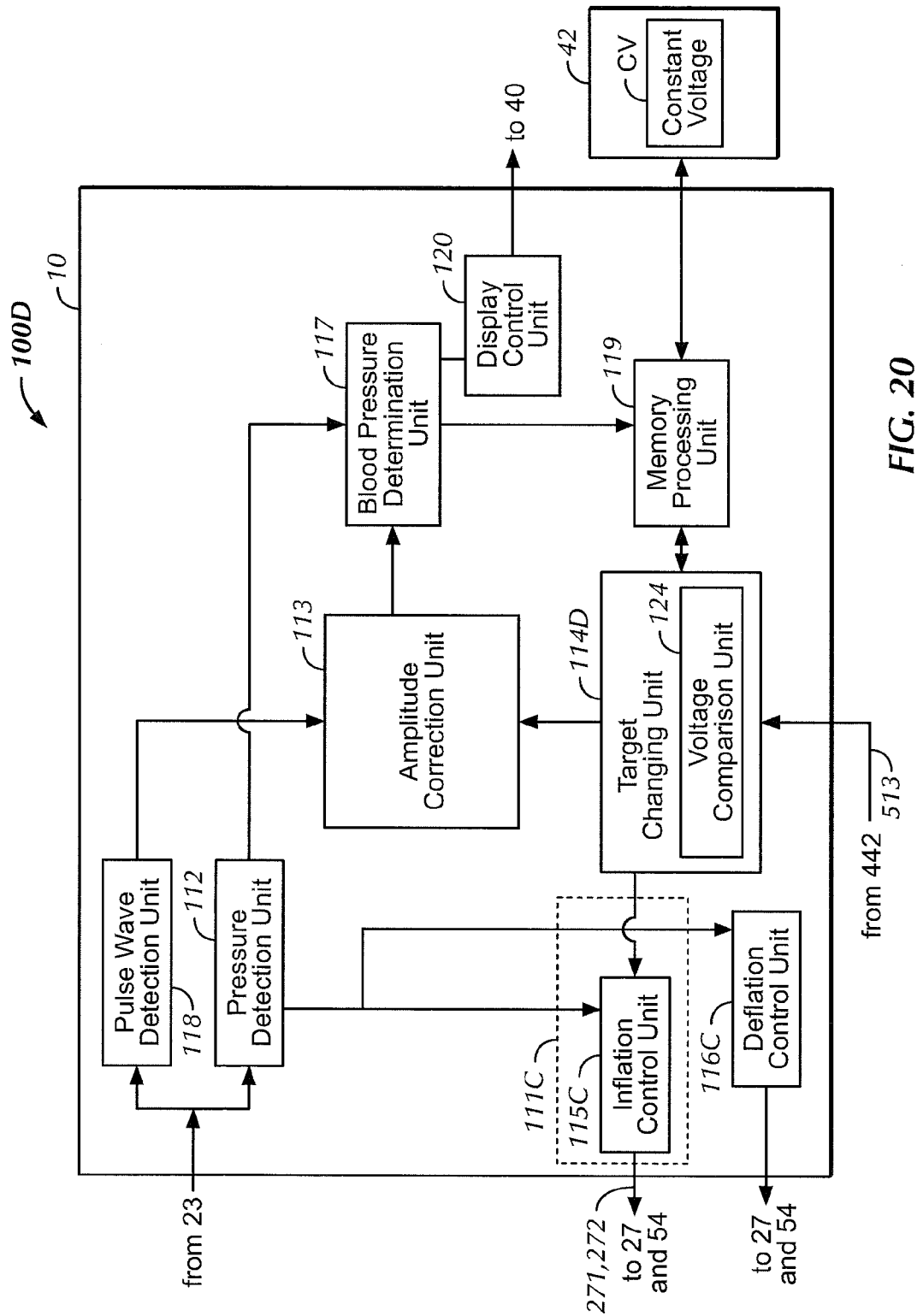
FIG. 20 is a block diagram illustrating the functional configuration of the electronic blood pressure meter according to a fifth embodiment.

The hardware configuration of an electronic blood pressure meter 100D according to the present embodiment is the same as that described in the fourth embodiment. FIG. 20 is a block diagram illustrating the functional configuration of the electronic blood pressure meter 100D according to the present fifth embodiment.

As shown in FIG. 20, the electronic blood pressure meter 100D has the same basic configuration as that shown in FIG. 17, but differs therefrom in that a target changing unit 114D having a voltage comparison unit 124 is provided instead of the target changing unit 114C and data CV specifying a constant voltage value (for example, 1.9 V) that is referred to in order to change the inflation speed target is stored in the memory unit 42. Accordingly, the differences will be described below.

The target changing unit 114D is inputted with the voltage data 513 during the blood pressure measurement, and uses the voltage comparison unit 124 to compare the cell voltage specified by the voltage data 513 with the constant voltage value specified by the data CV read out from the memory unit 42. Based on a result of the comparison, the target changing unit 114D lowers the present inflation speed target by a predetermined speed.

Figure 21:
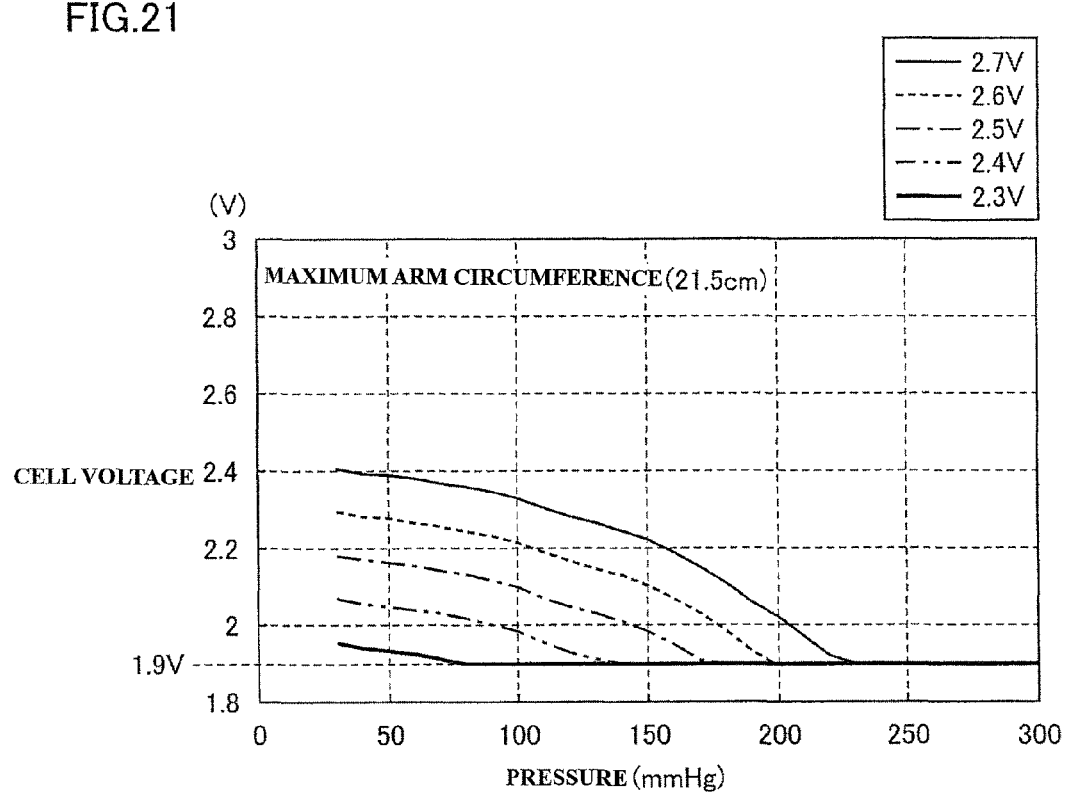
FIG. 21 is a graph illustrating a method for determining a constant voltage value according to the fifth embodiment.

FIG. 21 is a graph illustrating a method for deteimining the constant voltage value CV according to the present fifth embodiment. The vertical axis of the graph represents the cell voltage (unit: V), whereas the horizontal axis represents the cuff pressure (unit: mmHg). The graph indicates a change (a decrease) in the cell voltage accompanying a rise in the cuff pressure, based on experiments in which blood pressure measurement was carried out by the electronic blood pressure meter 100D using five batteries 443 having different cell voltages (2.7 V-2.3 V) in the case where the circumferential length of the measurement subject's arm was 21.5 cm. From the graph, the inventors confirmed that regardless of the initial cell voltage, the cell voltage will not change once the cell voltage reaches 1.9 V, or in other words, that the minimum necessary cell voltage CV for driving the piezoelectric pump 26 is 1.9 V. For the sake of simplicity, the descriptions of the present embodiment also assume that the circumferential length of the measurement subject's arm is the maximum arm circumference 21.5 cm (indicated in FIG. 21).

Processing Flowchart

Figure 22:
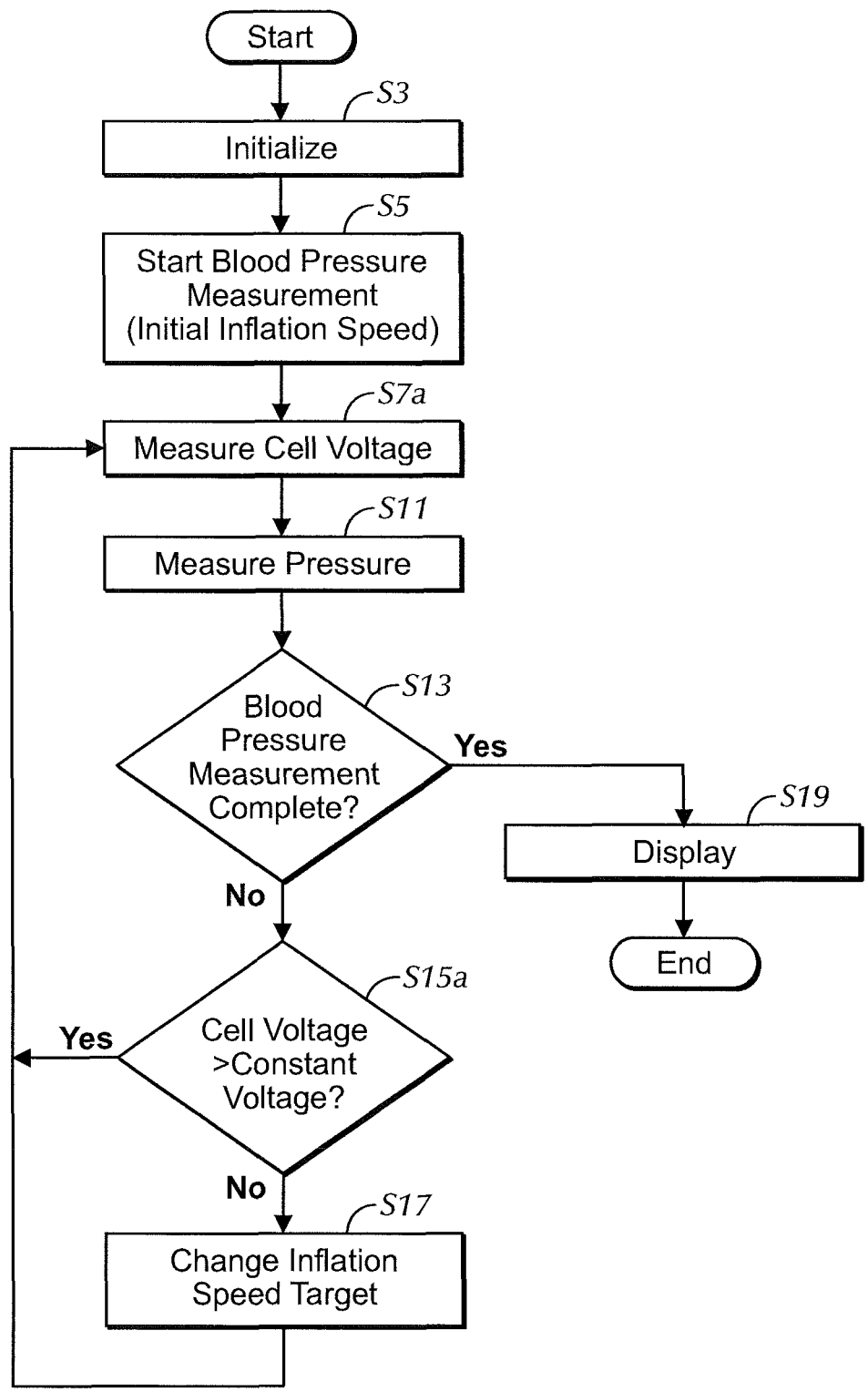
FIG. 22 is a flowchart illustrating a blood pressure measurement process according to the fifth embodiment.

FIG. 22 is a flowchart illustrating a blood pressure measurement process according to the present fifth embodiment. A program based on this flowchart is stored in the memory unit 42 in advance, and is read out from the memory unit 42 and executed by the CPU 10.

When the measurement subject manipulates the power switch 41A (or the measure switch 41B) while the cuff 20 is "properly wrapped" around the measurement area, the processes of steps S3 and S5 are carried out in the same manner as described above, and constant speed inflation is started in accordance with an initial inflation speed (5.5 mmHg/sec).

Thereafter, the target changing unit 114D is inputted with the voltage data 513 (step S7a). Meanwhile, the cuff pressure and the pulse wave amplitude are detected, and the blood pressure determination unit 117 carries out a process for measuring the blood pressure based on the detected cuff pressure and pulse wave amplitude (step S11). When it is determined that the blood pressure determination unit 117 has determined the blood pressure (YES in step S13), the processing advances to step S19.

However, when it is determined that the blood pressure has not been determined (NO in step S13), the voltage comparison unit 124 compares the voltage indicated by the voltage data 513 inputted in step S7a with the constant voltage specified by the data CV in the memory unit 42, and based on a result of the comparison, determines whether or not a condition (cell voltage>constant voltage) is met (step S15a). While it is determined that the condition is met (YES in step S15a), the process returns to step S7a, the same processing is carried out thereafter, and the constant speed inflation is continued at the present inflation speed target.

On the other hand, when it is determined that the aforementioned condition is not met (NO in step S15a), the target changing unit 114D decreases the current inflation speed target by a predetermined speed (step S17). The cuff pressure begins to increase at a constant speed in accordance with the post-change inflation speed target in the same manner as described above, and the voltage data 513 is inputted in step S7a. Thereafter, same processes as those described above are repeated.

In this manner, according to the present embodiment, the inflation speed target is reduced when the cell voltage drops below a constant voltage during the blood pressure measurement. Accordingly, the constant speed inflation can be continued while increasing the driving voltage that undergoes feedback control during the blood pressure measurement within a range in which there is an excess margin in the cell voltage.

Sixth Embodiment

In the fourth embodiment, a single table TB is referred to in order to determine the change start pressure; however, in the present sixth embodiment, the table referred to is switched based on the circumferential length of the measurement area. Through this, a higher measurement accuracy can be ensured by determining the change start pressure in a variable manner based on the circumferential length of the arm.

Figure 23:
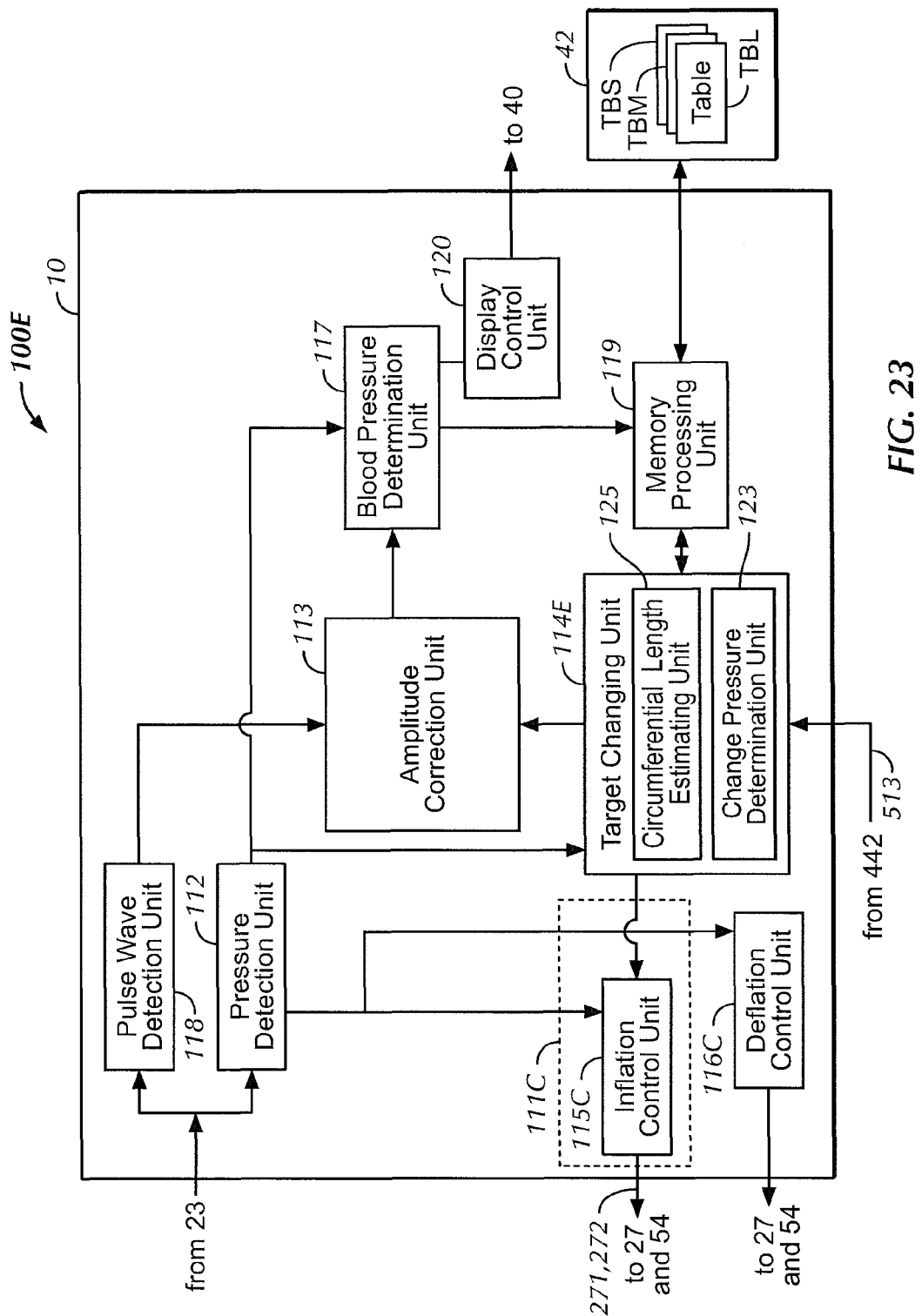
FIG. 23 is a block diagram illustrating the functional configuration of an electronic blood pressure meter according to a sixth embodiment.

The hardware configuration of an electronic blood pressure meter 100E according to the present embodiment is the same as that described in the fourth embodiment. FIG. 23 is a block diagram illustrating the functional configuration of the electronic blood pressure meter 100E according to the present sixth embodiment.

As shown in FIG. 23, the electronic blood pressure meter 100E has the same basic configuration as that shown in FIG. 17, but differs therefrom in that a target changing unit 114E is provided instead of the target changing unit 114C and tables TBL, TBM, and TBS that are referred to in order to change the inflation speed target are stored in the memory unit 42. Accordingly, the differences will be described below.

The tables TBL, TBM, and TBS in the memory unit 42 hold data obtained in advance through experimentation. The table TBL holds the data of the table TB (see FIG. 19) for the case where the circumferential length of the arm is "long". Likewise, the table TBM holds data for the case where the circumferential length of the arm is "medium", and the table TBS holds data for the case for the circumferential length of the arm is "short". The tables TBM and TBS hold the data in the same format as that shown in FIG. 19.

The target changing unit 114E includes a circumferential length estimating unit 125 having the same function as the aforementioned circumferential length estimating unit 401, and the change pressure determination unit 123. When the circumferential length of the measurement area is estimated by the circumferential length estimating unit 125, the change pressure determination unit 123 extracts the table, among the tables TBL, TBM, and TBS stored in the memory unit 42, that corresponds to the circumferential length obtained through the estimation (long, medium, or short). The extracted table is searched based on the cell voltage specified by the voltage data 513 obtained at the start of the blood pressure measurement. The change start pressure corresponding to the circumferential length of the arm can be determined based on a result of the search.

Specifically, even when the cell voltage is the same, it is thought that the inflation speed target will be changed before the measurement ends in the case where the circumferential length is "long", and thus the change start pressure is reduced; likewise, in the case where the circumferential length is "short", the change start pressure is increased. In this manner, the change start pressures corresponding to the circumferential lengths are in the relationship "long"<"medium"<"short".

Processing Flowchart

Figure 24:
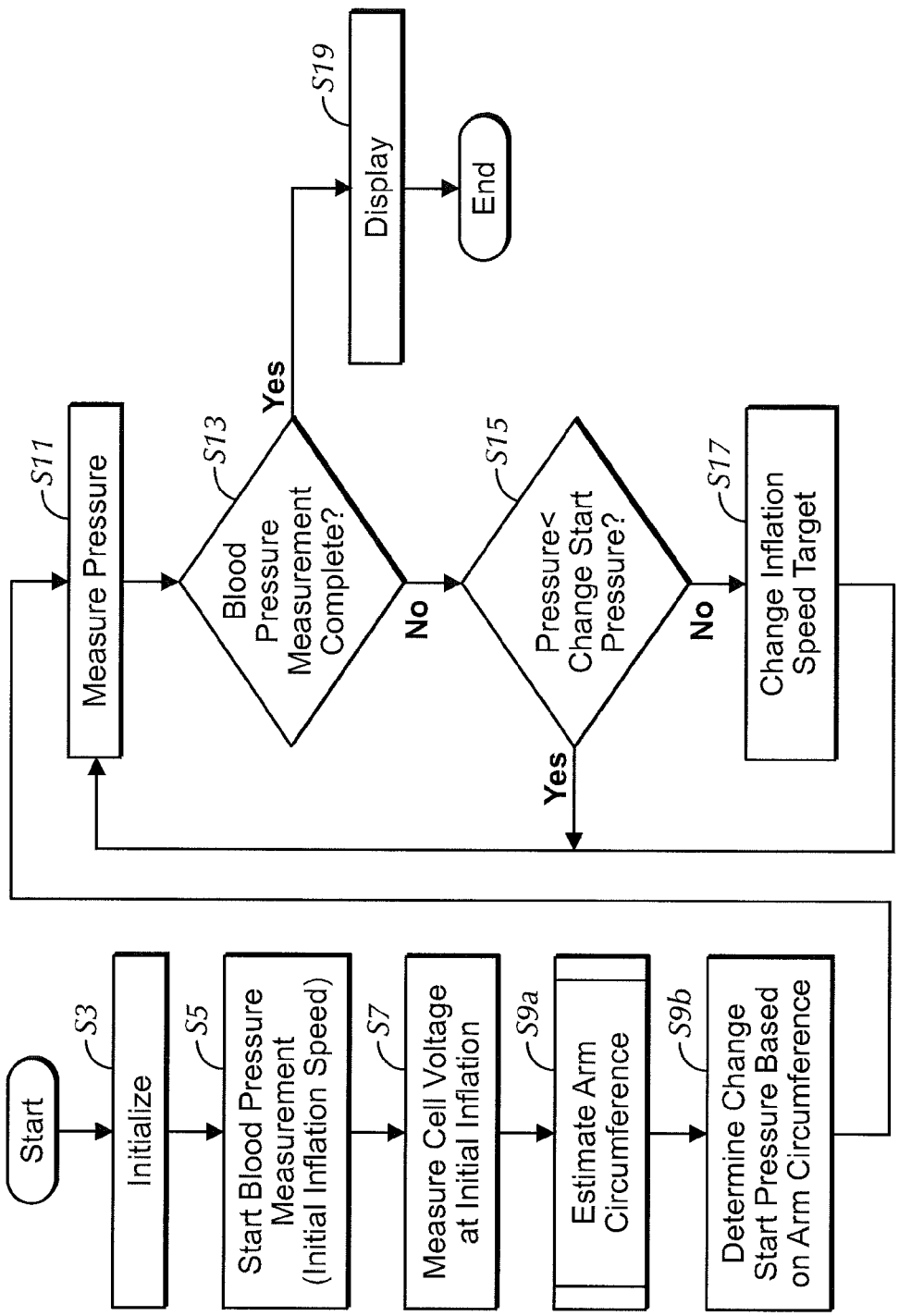
FIG. 24 is a flowchart illustrating a blood pressure measurement process according to the sixth embodiment.

FIG. 24 is a flowchart illustrating a blood pressure measurement process according to the present sixth embodiment. A program based on this flowchart is stored in the memory unit 42 in advance, and is read out from the memory unit 42 and executed by the CPU 10.

When the measurement subject manipulates the power switch 41A (or the measure switch 41B) while the cuff 20 is "properly wrapped" around the measurement area, the processes of steps S3 and S5 are carried out in the same manner as described before, after which the voltage data 513 is inputted into the target changing unit 114E and the cell voltage at the start of blood pressure measurement is obtained (step S7).

Then, when the constant speed inflation is started in accordance with the initial inflation speed (5.5 mmHg/sec), the circumferential length estimating unit 125 estimates the circumferential length of the measurement area around which the cuff 20 is wrapped (step S9a).

The change pressure determination unit 123 searches the memory unit 42 based on the cell voltage obtained in step S7 and the circumferential length estimated in step S9a, and extracts the table corresponding to the circumferential length. The change start pressure is then read out by searching the extracted table based on the cell voltage. Through this, the change start pressure is determined (step S9b).

Thereafter, the processes of steps S11 to S19 are carried out in the same manner as described above, and the blood pressure measurement ends.

Note that the obtainment of the circumferential length of the measurement area is not limited to the method employing the estimation process of step S9a; a circumferential length inputted by the measurement subject may be used, or circumferential lengths of measurement areas may be stored in advance in the memory unit 42 on a measurement subject-by-measurement subject basis and the circumferential length corresponding to a given measurement subject may be read out and obtained during measurement.

In this manner, according to the present embodiment, lower change start pressures are set for lower cell voltages when the circumferential length is the same and lower change start pressures are set for longer circumferential lengths when the cell voltage is the same, based on the cell voltage at the start of the blood pressure measurement and the circumferential length of the measurement area around which the cuff 20 is wrapped. Accordingly, the constant speed increase of the cuff pressure can be continued while the driving voltage, which undergoes feedback control, controls the driving of the pump within a range in which there is an excess margin for the cell voltage.

Seventh Embodiment

In the fourth embodiment, the change start pressure is determined based on the cell voltage measured at the initial stage of inflation when the blood pressure measurement is started; in the present embodiment, however, the change start pressure is varied in accordance with a difference between a BL ("battery low") voltage set for the battery 443 and a cell voltage obtained at the initial inflation.

Here, "battery low" refers to a required voltage determined in accordance with the design specifications of the electronic blood pressure meter, and specifies a cell voltage required in order to ensure that the electronic blood pressure meter operates normally. Data BLV specifying a value set for the BL voltage is stored in advance in the memory unit 42 of each electronic blood pressure meter.

Figure 25:
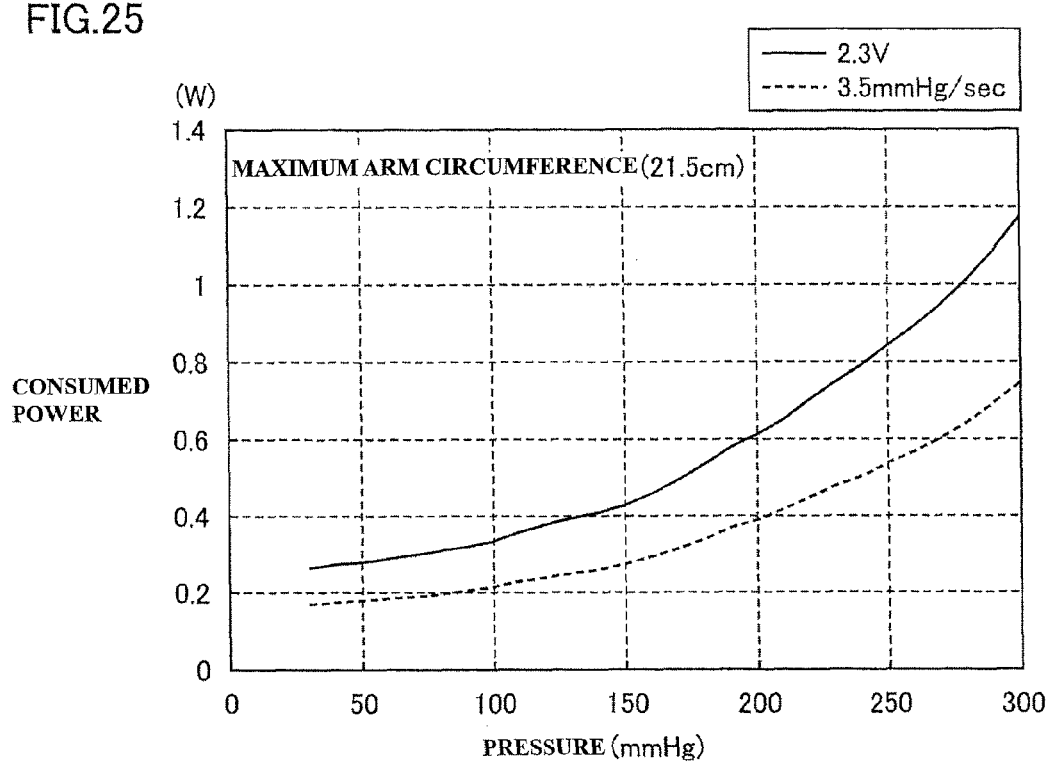
FIG. 25 is a graph illustrating a relationship between power consumed by an electronic blood pressure meter and a cuff pressure.
Figure 26:
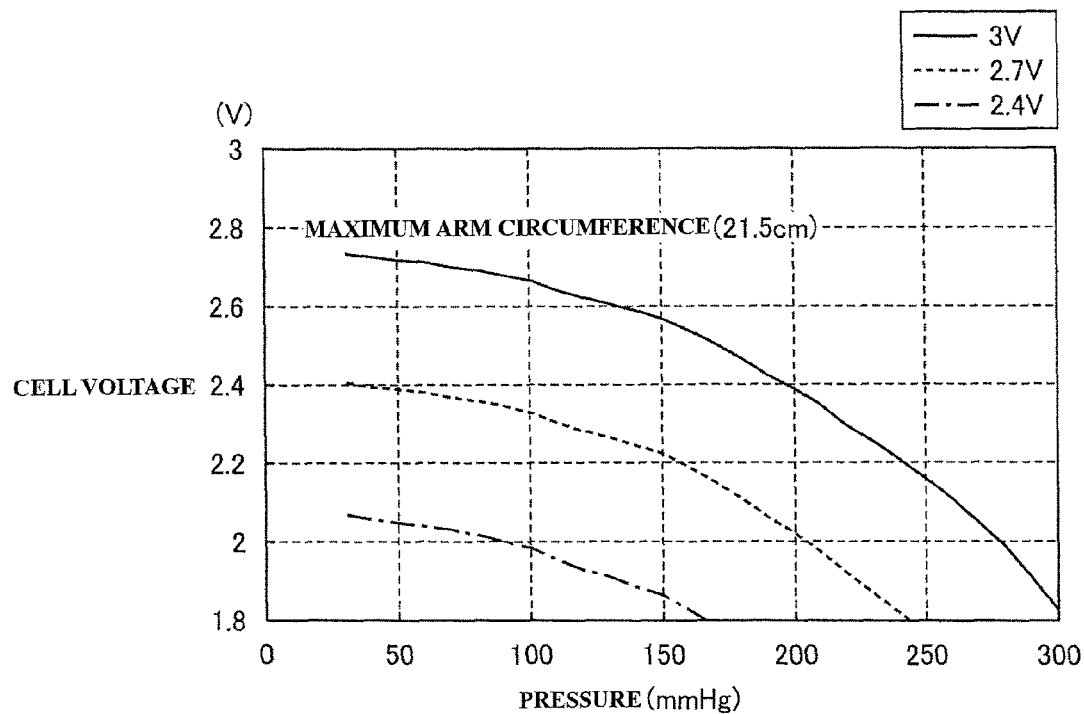
FIG. 26 is a graph illustrating a relationship between a decrease in the voltage of the battery in an electronic blood pressure meter and a cuff pressure.

FIG. 25 is a graph indicating a relationship between power consumption of the electronic blood pressure meter and the cuff pressure, where the vertical axis of the graph represents the power consumption (unit: W) and the horizontal axis represents the cuff pressure (unit: mmHg). FIG. 26, meanwhile, is a graph indicating a relationship between a drop in the voltage of a battery of the electronic blood pressure meter and the cuff pressure, where the vertical axis of the graph represents the cell voltage (unit: V) and the horizontal axis represents the cuff pressure (unit: mmHg).

In the case where the cuff pressure has been increased at a predetermined cell voltage (2.3 V), it can be seen from the graph in FIG. 25 that an increased amount of power is consumed as the cuff pressure rises and there is an increased drop in the voltage in the battery 443. It is therefore necessary to set the BL voltage higher in order to increase the cuff pressure to a pressure required for measurement; however, increasing the BL voltage reduces the lifespan of the battery 443. Meanwhile, while the inflation speed may be reduced (to, for example, 3.5 mmHg/sec) in order to reduce the amount of power consumed (see FIG. 25), doing so increases the time required for the measurement. Accordingly, in the present embodiment, the BL voltage is set in a variable manner based on a relationship between the power consumed and the inflation speed obtained through experimentation, and is stored in the memory unit 42 as the data BLV.

Figure 27:
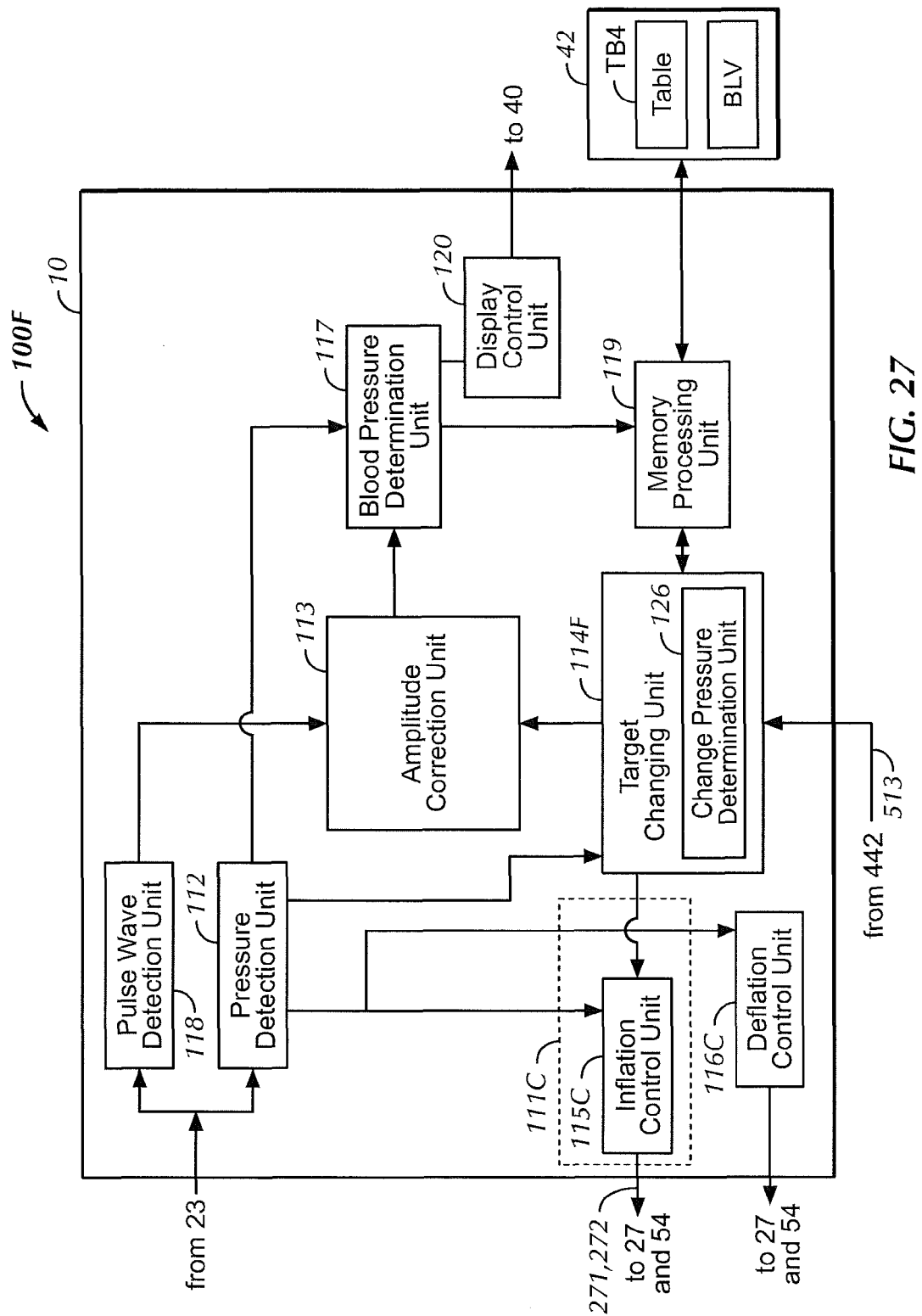
FIG. 27 is a diagram illustrating the functional configuration of an electronic blood pressure meter according to a seventh embodiment.
Figure 28:
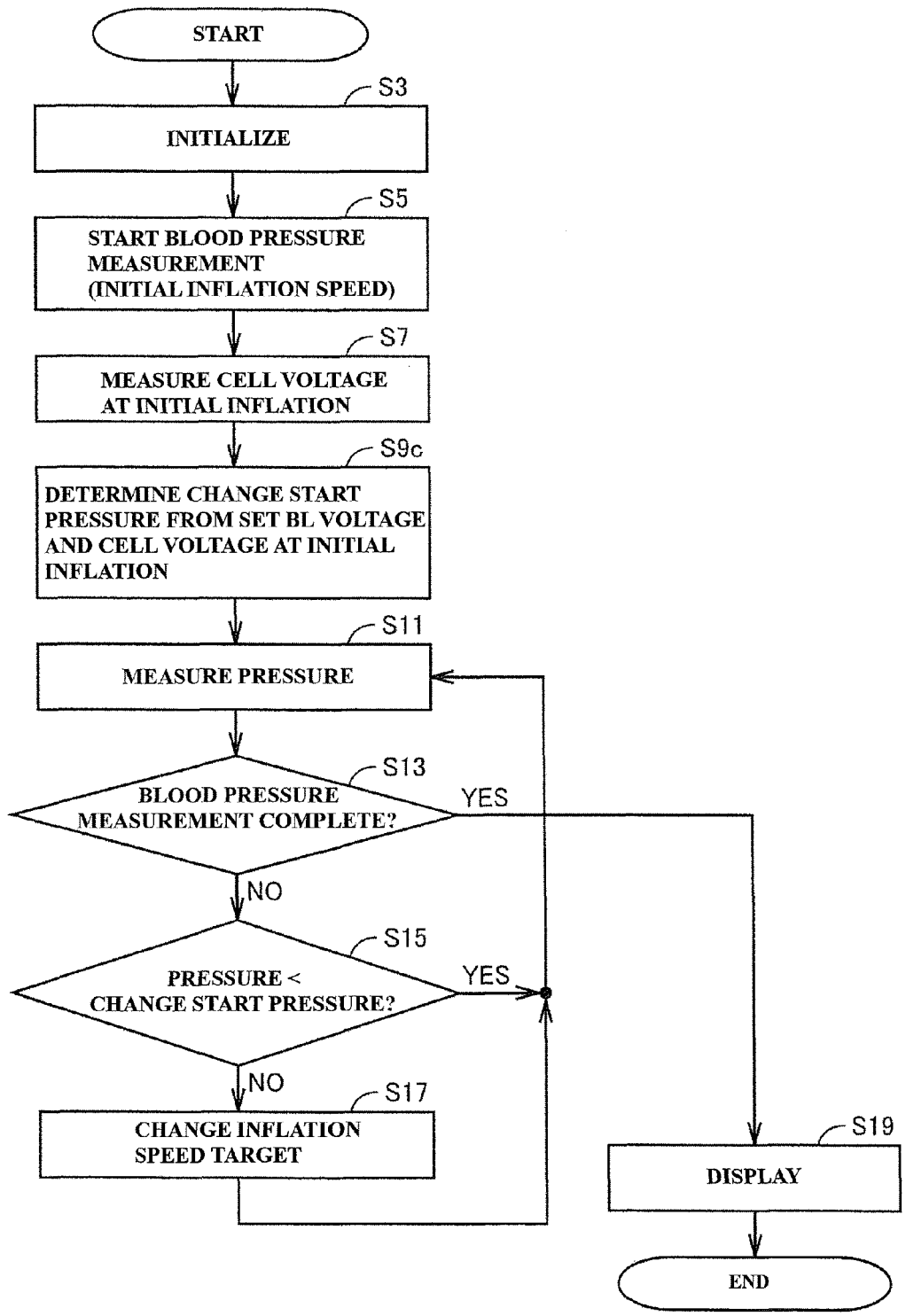
FIG. 28 is a flowchart illustrating processing according to the seventh embodiment.
Figure 29:
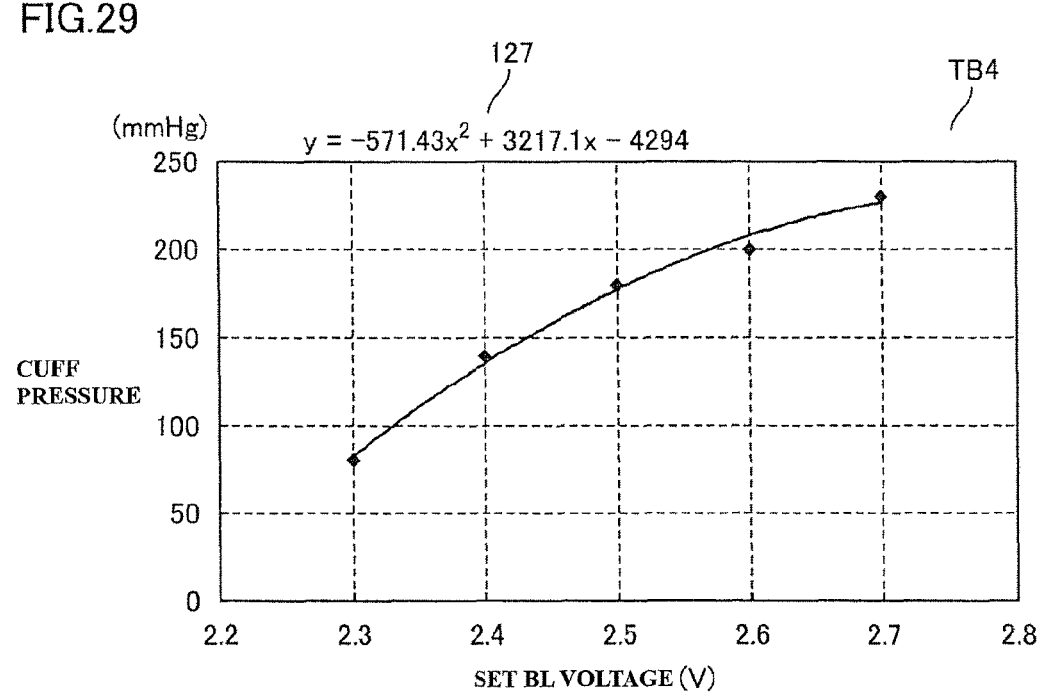
FIG. 29 is a graph schematically illustrating the content of a table according to the seventh embodiment.

FIG. 27 illustrates the functional configuration of an electronic blood pressure meter 100F according to the present seventh embodiment, FIG. 28 illustrates a processing flowchart according to the present embodiment, and FIG. 29 is a graph schematically illustrating the content of a table TB4 referred to in order to determine the change start pressure according to the present embodiment. The graph in FIG. 29 was obtained through experiments performed using the electronic blood pressure meter 100F.

The graph in FIG. 29 illustrates a case where the cell voltage obtained during the initial inflation is a predetermined value and constant speed inflation has been continued at the initial inflation speed target (5.5 mmHg/sec), and uses approximated curves to illustrate the relationship between the BL voltage and the maximum value of the cuff pressure at which the constant speed inflation can be continued, for each set BL voltage.

The vertical axis in the graph represents the cuff pressure detected by the pressure detection unit 112 (unit mmHg/sec), the horizontal axis represents the set BL voltage indicated by the data BLV (unit: V), and the approximated curves are represented by a formula 127. According to this graph, in the case where the set BL voltage is, for example, 2.5 V, the constant speed inflation can be carried out up to 175 mmHg, and thus a change pressure determination unit 126 reduces the initial inflation speed target when it is determined that the cuff pressure from the pressure detection unit 112 is 175 mmHg Such data obtained through experimentation is held in the table TB4. Specifically, the table TB4 holds a plurality of sets of cell voltages and set BL voltages, along with maximum values of the cuff pressure at which the constant speed inflation can be continued at the initial inflation speed target that correspond to each of the stated sets.

As shown in FIG. 27, the electronic blood pressure meter 100F has the same basic configuration as that shown in FIG. 17, but differs therefrom in that a target changing unit 114F having the change pressure determination unit 126 is provided instead of the target changing unit 114C, and in that the table TB4 and the data BLV referred to in order to change the inflation speed target are stored in the memory unit 42. Accordingly, the differences will be described below.

The change pressure determination unit 126 searches the table TB4 for a set composed of a cell voltage of the battery 443 based on the voltage data 513 and a set BL voltage specified by the data BLV read out from the memory unit 42, and reads out a cuff pressure corresponding to the set from the table TB4 based on a result of the search. Through this, the change start pressure is determined. The target changing unit 114F compares the cuff pressure inputted from the pressure detection unit 112 during the blood pressure measurement with the determined change start pressure, and reduces the inflation speed target based on a result of the comparison.

Processing Flowchart

FIG. 28 is a flowchart illustrating a blood pressure measurement process according to the present seventh embodiment. A program based on this flowchart is stored in the memory unit 42 in advance, and is read out from the memory unit 42 and executed by the CPU 10.

When the measurement subject manipulates the power switch 41A (or the measure switch 41B) while the cuff 20 is "properly wrapped" around the measurement area, the processes of steps S3 and S5 are carried out in the same manner as described before, after which the voltage data 513 is inputted into the target changing unit 114F and the cell voltage at the start of blood pressure measurement is obtained (step S7); furthermore, the change pressure determination unit 126 determines the change start pressure based on the initial cell voltage and the set BL voltage specified by the data BLV as described earlier (step S9c).

Thereafter, when the constant speed inflation is started in accordance with the initial inflation speed (5.5 mmHg/sec), the processes of steps S11 to S19 are carried out in the same manner as described above, and the blood pressure measurement ends.

Note that the change start pressure is not limited to being determined by searching the table TB4, and may instead be calculated based on the formula 127. In other words, the formula 127 may be prepared for each of sets composed of a cell voltage and a set BL voltage specified by the data BLV, and the change start pressure may then be determined through a calculation based on the formula 127.

In addition, the change start pressure may be determined based on a difference between the initial cell voltage and the set BL voltage specified by the data BLV.

In this manner, according to the present embodiment, if the initial cell voltage is the same, the change start pressure can be set to a higher pressure as the set BL voltage specified by the data BLV increases (see FIG. 27), which makes it possible to reduce the number of times the inflation speed target is changed during the blood pressure measurement; this in turn makes it possible to suppress errors from occurring in the pulse wave amplitude due to changes in the inflation speed target. Furthermore, if the initial cell voltage is the same, the change start pressure can be set to a lower pressure as the set BL voltage specified by the data BLV decreases (see FIG. 29), which makes it possible to continue the constant speed inflation while avoiding a situation where the driving voltage that undergoes feedback control exceeds the set BL voltage and the speed cannot be further increased, making it impossible to increase the cuff pressure at a constant speed.

Eighth Embodiment

According to an eighth embodiment, when it is determined, based on the change start pressure determined as described in the aforementioned embodiments, that the amount of time required for the blood pressure measurement will exceed a specified time, a notification to that effect is outputted. This enables the measurement subject to confirm that a long measurement time does not mean that the electronic blood pressure meter has malfunctioned.

Figure 30:
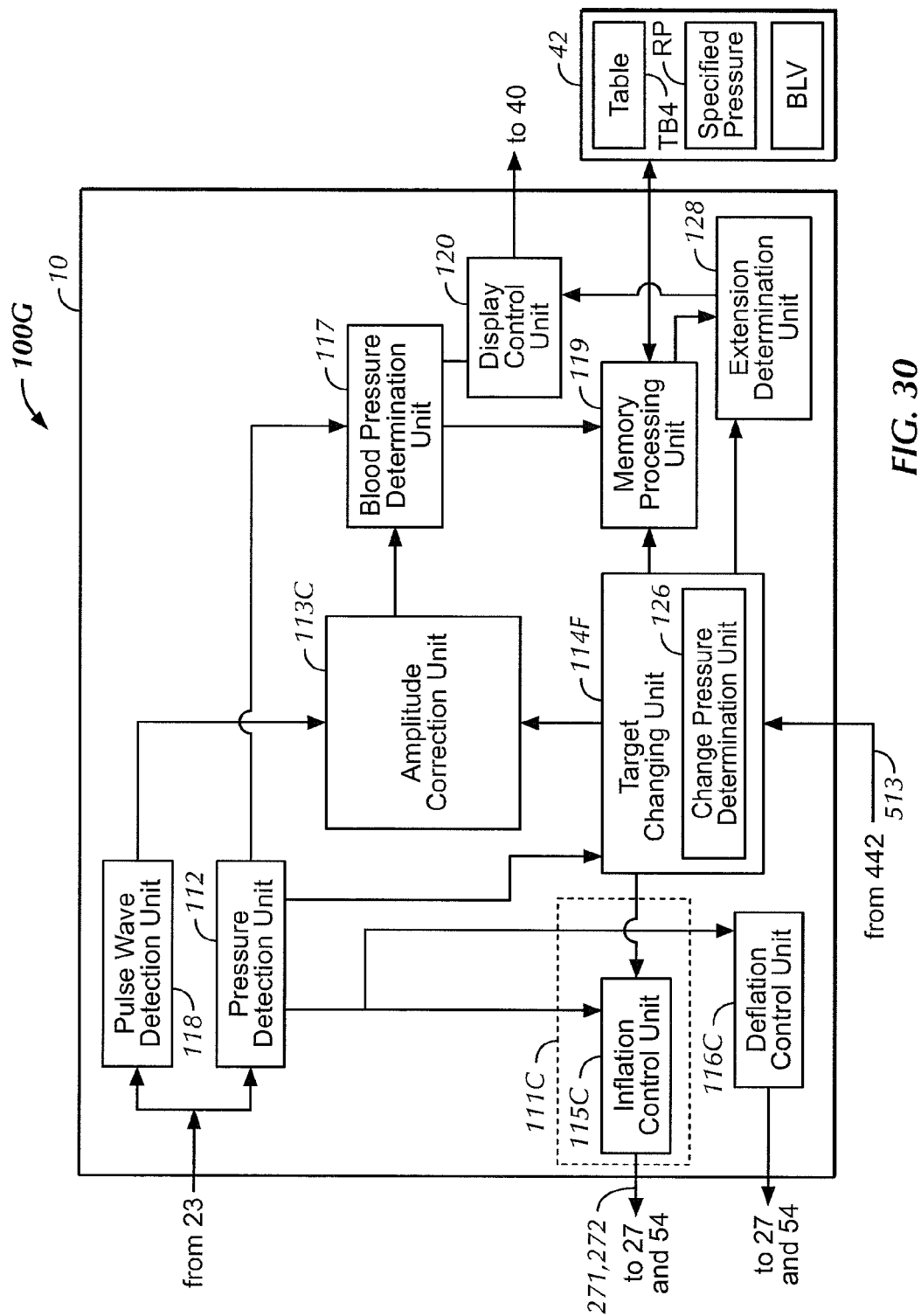
FIG. 30 is a diagram illustrating the functional configuration of an electronic blood pressure meter according to an eighth embodiment.
Figure 31:
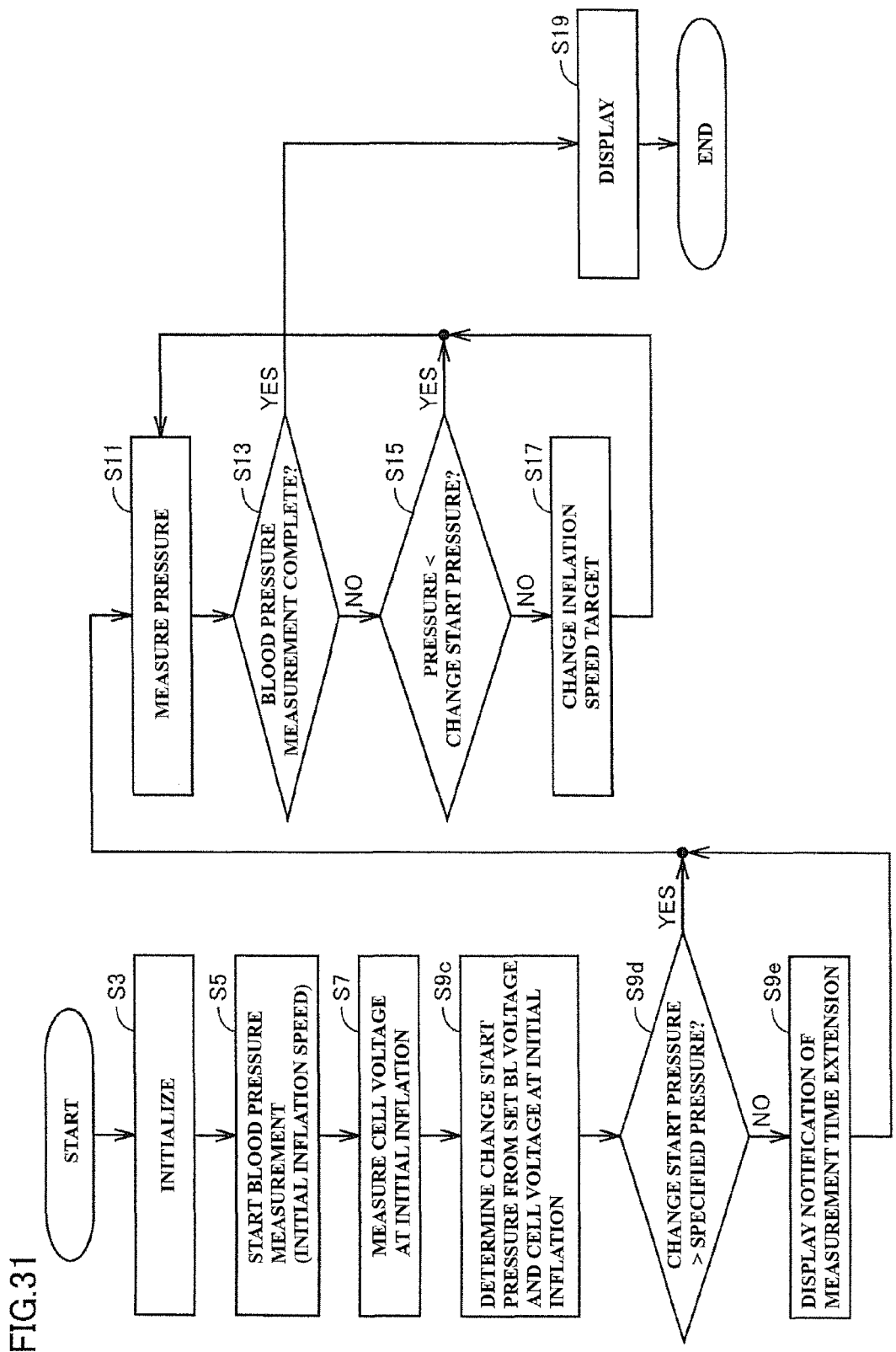
FIG. 31 is a flowchart illustrating processing according to the eighth embodiment.
Figure 32:
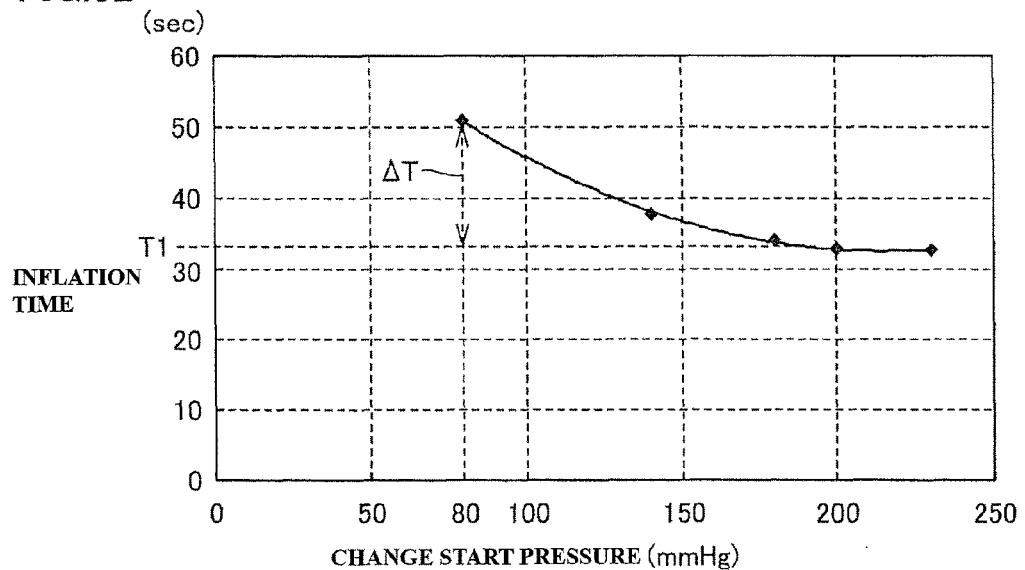
FIG. 32 is a graph illustrating a relationship between a pressure at the start of a change and an inflation time (measurement time) according to the eighth embodiment.
Figure 33:
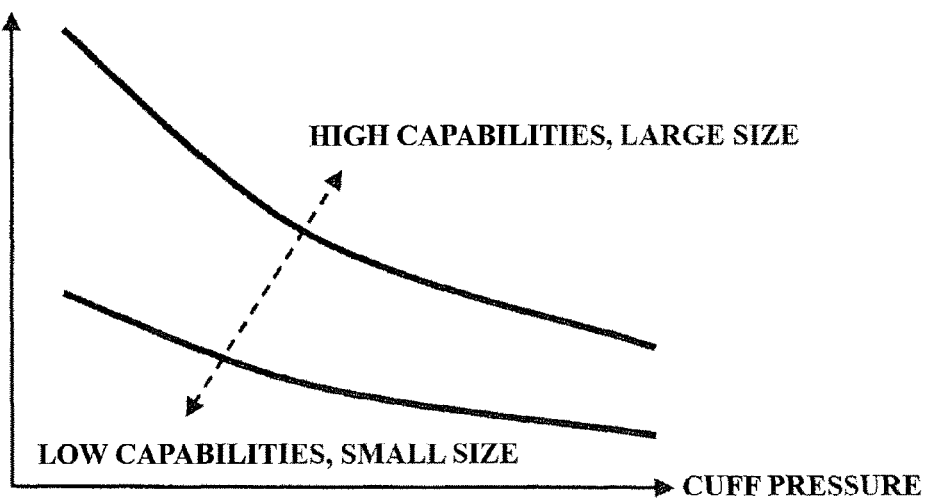
FIG. 33 schematically illustrates a relationship between a pump output flow rate and a cuff pressure in a conventional blood pressure meter.

FIG. 30 illustrates the functional configuration of an electronic blood pressure meter 100G according to the present eighth embodiment, FIG. 31 illustrates a processing flowchart according to the present embodiment, and FIG. 32 is a graph illustrating a relationship between the change start pressure and the inflation time (measurement time) as an approximated curve according to the present embodiment. The graph in FIG. 32 was obtained through experiments performed using the electronic blood pressure meter 100G Note that it is assumed here that the cell voltage of the battery 443 and the set BL voltage are sufficiently high.

In FIG. 32, the vertical axis of the graph represents the inflation time (unit: sec), whereas the horizontal axis represents the change start pressure (unit: mmHg). A relationship between the cuff pressure detected when the inflation speed target has been changed at an appropriate timing while continuing the constant speed inflation at the initial inflation speed target (5.5 mmHg/sec) (that is, the change start pressure) and the inflation time corresponding to that cuff pressure is represented by the approximated curve in the graph. The inflation time corresponding to the cuff pressure (the change start pressure) refers to an amount of time taken from the start of measurement to the end of measurement (from the start of inflation to the end of inflation (the start of exhaust)) in the case where the inflation target speed (5.5 mmHg/sec) has been changed (reduced) at the stated change start pressure.

According to FIG. 32, the inflation time differs by $\Delta T$ between the case where the measurement ends without the initial inflation speed target being changed and the case where the inflation is started at the initial inflation speed target, the inflation speed target is changed at the change start pressure (80 mmHg), and the measurement then ends. Accordingly, in the present embodiment, an inflation time T1 for the case where, for example, the measurement ends without changing the initial inflation speed target is used, and the specified time is calculated as $(T1+(\Delta T/2))$. Then, the change start pressure corresponding to the calculated specified time is searched out from the data in the graph shown in FIG. 32, and the change start pressure read out as a result of the search is set as a specified pressure.

As shown in FIG. 30, the electronic blood pressure meter 100G has the same basic configuration as that shown in FIG. 25, but differs therefrom in that an extension determination unit 128 for determining that the measurement time will be extended is additionally provided and data RP indicating the specified pressure is stored in the memory unit 42 in addition to the table TB4 and the data BLV. Accordingly, the differences will be described below.

The extension determination unit 128 is inputted with the change start pressure determined by the change pressure determination unit 126, compares the inputted change start pressure with the specified pressure indicated by the data RP read out from the memory unit 42, and based on a result of the comparison, displays a message reading "measurement time will be extended" in the display unit 40 via the display control unit 120. Note that the output is not limited to a display, and may employ audio instead.

Processing Flowchart

FIG. 31 is a flowchart illustrating a blood pressure measurement process according to the present eighth embodiment. A program based on this flowchart is stored in the memory unit 42 in advance, and is read out from the memory unit 42 and executed by the CPU 10.

When the measurement subject manipulates the power switch 41A (or the measure switch 41B) while the cuff 20 is "properly wrapped" around the measurement area, the processes of steps S3 to S7 are carried out in the same manner as described before, after which the change pressure determination unit 126 determines the change start pressure based on the initial cell voltage and the set BL voltage specified by the data BLV as described earlier (step S9c).

The extension determination unit 128 is inputted with the change start pressure from the change pressure determination unit 126, and compares the inputted change start pressure with the specified pressure indicated by the data RP read out from the memory unit 42. If it is determined based on a result of the comparison that a condition (change start pressure<specified pressure) is met (YES in step S9d), the display indicating that the measurement time will be extended is not made; the constant speed inflation is started in accordance with the initial inflation speed (5.5 mmHg/sec), the processes of steps S11 to S19 are carried out in the same manner as described above, and the blood pressure measurement ends.

On the other hand, if it is determined based on the result of the comparison that the condition (change start pressure<specified pressure) is not met (NO in step S9d), the extension determination unit 128 causes the display unit 40 to display the message "measurement time will be extended" via the display control unit 120 (step S9e). Thereafter, the processing moves to steps S11 and on.

Although the foregoing descriptions describe a case where the inflation speed target is changed using the method described in the seventh embodiment, the determination made by the extension determination unit 128 and the output of the notification that the measurement time will be extended can be applied even in the case where the inflation speed target is changed using the methods described in the other embodiments.

In this manner, according to the present embodiment, when the measurement is started and it is thought that the inflation time will exceed the specified time due to the inflation speed target being changed, a notification to that effect is outputted. Through this, it is possible to eliminate unease on the part of the measurement subject due to long measurement times, which in turn makes it possible to avoid fluctuations in the blood pressure caused by such unease.

Variations

Although the change start pressure for changing the inflation speed target is determined using the cell voltage during the blood pressure measurement in the fourth to eighth embodiments, the amount of power consumed by the electronic blood pressure meter may be used instead of the cell voltage. Alternatively, the amount of power consumed may be calculated based on the consumed current value inputted from the consumed current measurement circuit 28, using a predetermined conversion formula.

Meanwhile, the post-change inflation speed target may be changed based on information indicating the blood pressure level of the measurement subject as described in the second embodiment, even in the case where the change start pressure is determined using the cell voltage. Alternatively, the inflation speed target may be changed based on the obtained circumferential length as described in the third embodiment.

Note that the embodiments disclosed above are to be understood as being in all ways exemplary and in no way limiting. The scope of the present invention is defined not by the aforementioned descriptions but by the scope of the appended claims, and all changes that fall within the same essential spirit as the scope of the claims are intended to be included therein as well.

REFERENCE SIGNS LIST 20 cuff
51 pump
52 valve
53 pump driving circuit
54 valve driving circuit
100, 100A, 100B electronic blood pressure meter
111 driving control unit
112 pressure detection unit
113 amplitude correction unit
114, 114A, 114B target changing unit
115 inflation control unit
116 deflation control unit
117 blood pressure determination unit
118 pulse wave detection unit
119 memory processing unit
120 display control unit
121 pulse wave counting unit
122 target determination unit
402 correction coefficient determination unit
511 driving voltage
512 upper-limit driving voltage
123, 126 change pressure determination unit
124 voltage comparison unit
125, 401 circumferential length estimating unit
128 extension determination unit
271 voltage control signal
272 frequency control signal
273 vibration control voltage signal

The invention claimed is:

1. An electronic blood pressure meter comprising:
a cuff to be wrapped around a measurement area of a measurement subject;
a pump that outputs a fluid into the cuff;
a control unit that controls the pump so that a pressure in the cuff is increased at an inflation speed target in accordance with a driving voltage;
a pressure detection unit that detects a cuff pressure signal indicating a cuff pressure in the cuff;
a blood pressure calculation unit that calculates a blood pressure value based on a pulse wave superimposed on the cuff pressure signal detected by the pressure detection unit;
a target changing unit that varies the inflation speed target during an inflation process in which the cuff pressure begins to increase at an initial inflation speed target and continues to increase,
wherein the target changing unit varies the inflation speed target so that the driving voltage measured during the inflation process stays within a voltage range corresponding to a range in which the pump is capable of output; and
a cell voltage measurement unit that measures a voltage of a battery for supplying power to the various units in the electronic blood pressure meter as the driving voltage,
wherein the target changing unit includes a change pressure determination unit that determines a cuff pressure at which the inflation speed target is to be varied based on the measured voltage of the battery, and
wherein the target changing unit varies the inflation speed target when, during the inflation process, the cuff pressure signal detected by the pressure detection unit indicates the determined cuff pressure.

2. The electronic blood pressure meter according to claim 1, wherein the change pressure determination unit determines the cuff pressure at which the inflation speed target is to be varied based on the voltage of the battery measured at the start of the inflation.

3. The electronic blood pressure meter according to claim 1,
wherein the change pressure determination unit determines the cuff pressure at which the inflation speed target is to be varied based on a difference between a predetermined voltage required for the battery to ensure the electronic blood pressure meter operates normally and the measured voltage of the battery.

4. The electronic blood pressure meter according to claim 1,
wherein information indicating a blood pressure level of the measurement subject is obtained, and
wherein the target changing unit changes the inflation speed target based on the obtained information.

5. The electronic blood pressure meter according to claim 4, further comprising:
a pulse wave detection unit that detects a pulse wave superimposed on the cuff pressure signal detected by the pressure detection unit,
wherein the target changing unit obtains the information indicating the blood pressure level of the measurement subject based on a number of pulse waves detected by the pulse wave detection unit during a period spanning from when the inflation starts to when a cuff pressure in a predetermined range is detected.

6. The electronic blood pressure meter according to claim 1 further comprising an extension determination unit that determines whether the measurement will take a longer amount of time based on a result of comparing a change start pressure with a predetermined pressure.

7. The electronic blood pressure meter according to claim 1,
wherein the blood pressure calculation unit changes a pulse wave amplitude to correct an error caused by changing the inflation speed target, and calculates the blood pressure based on the cuff pressure and the post-change pulse wave amplitude.

8. The electronic blood pressure meter according to claim 7,
wherein the blood pressure calculation unit includes a coefficient determination unit for determining a coefficient for the correction based on the pre- and post-change inflation speed targets, and
wherein the blood pressure calculation unit calculates the post-change pulse wave amplitude based on a pre-change pulse wave amplitude using the determined coefficient.

9. The electronic blood pressure meter according to claim 8,
wherein the coefficient determination unit determines the coefficient based on a ratio between the pre-change inflation speed target and the post-change inflation speed target.

10. The electronic blood pressure meter according to claim 9, further comprising:
a circumferential length obtainment unit that obtains a circumferential length of the measurement area,
wherein the coefficient determination unit determines the coefficient based on the obtained circumferential length and the ratio between the pre-change inflation speed target and the post-change inflation speed target.

11. An electronic blood pressure meter comprising:
a cuff that is configured to be wrapped around a measurement area of a measurement subject;
a pump that outputs a fluid into the cuff;
a control unit that controls the pump so that a pressure in the cuff is increased at an inflation speed target in accordance with a driving voltage;
a pressure detection unit that detects a cuff pressure signal indicating a cuff pressure in the cuff;
a blood pressure calculation unit that calculates a blood pressure value based on a pulse wave superimposed on the cuff pressure signal detected by the pressure detection unit; and
a target changing unit that varies the inflation speed target during an inflation process in which the cuff pressure begins to increase at an initial inflation speed target and continues to increase,
wherein the target changing unit varies the inflation speed target so that the an amount of consumed power measured during the inflation process stays within a consumed power range corresponding to a range in which the pump is capable of output,
wherein the target changing unit includes a change pressure determination unit that determines a cuff pressure at which the inflation speed target is to be varied based on the amount of consumed power measured, and
wherein the target changing unit varies the inflation speed target when, during the inflation process, the cuff pressure signal detected by the pressure detection unit indicates the determined cuff pressure.

* * * * *